US012215975B2

(12) United States Patent
Wang et al.

(10) Patent No.: US 12,215,975 B2
(45) Date of Patent: Feb. 4, 2025

(54) METHODS AND SYSTEMS FOR ADAPTIVE PEDESTRIAN INERTIAL NAVIGATION

(71) Applicant: The Regents of the University of California, Oakland, CA (US)

(72) Inventors: Yusheng Wang, Irvine, CA (US); Andrei M. Shkel, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 775 days.

(21) Appl. No.: 17/395,706

(22) Filed: Aug. 6, 2021

(65) Prior Publication Data

US 2022/0042801 A1    Feb. 10, 2022

Related U.S. Application Data

(60) Provisional application No. 63/063,034, filed on Aug. 7, 2020.

(51) Int. Cl.
*G01C 21/16*    (2006.01)
*A61B 5/11*    (2006.01)
(Continued)

(52) U.S. Cl.
CPC ............ *G01C 21/166* (2020.08); *A61B 5/112* (2013.01); *G01C 22/006* (2013.01); *G01C 21/206* (2013.01)

(58) Field of Classification Search
CPC .. G01C 21/166; G01C 22/006; G01C 21/206; A61B 5/112
See application file for complete search history.

(56) References Cited

U.S. PATENT DOCUMENTS

| 2012/0089330 A1* | 4/2012 | Hesch | G01C 22/006 |
| | | | 703/13 |
| 2012/0183179 A1* | 7/2012 | Susca | G01C 23/005 |
| | | | 382/107 |

(Continued)

FOREIGN PATENT DOCUMENTS

| CN | 104729507 B | * | 1/2018 | ............. G01C 21/16 |
| KR | 20160098823 A | * | 8/2016 | |

OTHER PUBLICATIONS

CN104729507B (Year: 2018).*
(Continued)

*Primary Examiner* — Manish S Shah
*Assistant Examiner* — Sharad Timilsina
(74) *Attorney, Agent, or Firm* — John P. Teresinski; Stites & Harbison, PLLC

(57) ABSTRACT

Processes and systems for adaptive pedestrian inertial navigation are provided. Configurations can adjust to various navigation scenarios, including different floor types and different gait paces. A combination of IMU data partition, principal component analysis (PCA), and artificial neural network may be used to perform the floor type detection. Floor type results may be used in the multiple-model extended Kalman filter. In each extended Kalman filter, an adaptive threshold is used for the stance phase detection to enable the detector to adjust to gait frequency without tuning design parameters during navigation. A floor type classification of high accuracy is demonstrated, and the position error in a velocity-changing navigation system using adaptive threshold is reduced.

20 Claims, 19 Drawing Sheets

(51) Int. Cl.
  *G01C 21/20* (2006.01)
  *G01C 22/00* (2006.01)

(56) References Cited

U.S. PATENT DOCUMENTS

| | | | | |
|---|---|---|---|---|
| 2014/0203971 A1* | 7/2014 | Taylor, Jr | ............ | G01C 21/1652 |
| | | | | 342/458 |
| 2017/0363427 A1* | 12/2017 | Naimark | ................ | A61B 5/486 |
| 2019/0388728 A1* | 12/2019 | Wang | ................ | A63B 24/0006 |
| 2020/0147451 A1* | 5/2020 | Frank | .................... | A61B 5/112 |

OTHER PUBLICATIONS

Yusheng Wang and Andrei M. Shkel, Pedestrian Inertial Navigation with Self-Contained Aiding, Wiley-IEEE Press; https://www.amazon.com/Pedestrian-Inertial-Navigation-Self-Contained-Sensors/dp/111969955X/ref=sr_1_1?dchild=1&keywords=Shkel&qid=1628017862&s=books&sr=1-1, excerpt from a book, 25 pages.
Yusheng Wang and Andrei M. Shkel, Learning-Based Floor Type Identification in the ZUPT-Aided Pedestrian Inertial Navigation, IEEE Sensors Letters, doi: 10.1109/LSENS.2021.3058360, 1 page.
Yusheng Wang, Chi-Shih Jao, and Andrei M. Shkel Scenario-Dependent ZUPT-Aided Pedestrian Inertial Navigation with Sensor Fusion, Journal of Gyroscopy and Navigation, vol. 12, issue 1, 2021, 1 page.

* cited by examiner

METHODS AND SYSTEMS FOR ADAPTIVE PEDESTRIAN INERTIAL NAVIGATION

CROSS REFERENCE TO RELATED APPLICATION

This application claims priority to U.S. provisional application No. 63/063,034 titled METHOD AND SYSTEM FOR ADAPTIVE PEDESTRIAN INERTIAL NAVIGATION filed on Aug. 7, 2020, the content of which is expressly incorporated by reference in its entirety.

STATEMENT OF GOVERNMENT SUPPORT

This invention was made with Government support under Grant No. 70NANB17H192, awarded by the National Institutes of Standards Technology. The Government has certain rights in the invention.

FIELD

The present disclosure generally relates to systems and methods of pedestrian inertial navigation using an inertial measurement unit (IMU) including learning based floor-type identification and adaptive detection of stance phases in human gait cycles.

BACKGROUND

Pedestrian inertial navigation systems have been developed using microelectromechanical systems (MEMS) based inertial measurement units (IMUs). IMUs may have beneficial characteristics including desirable noise characteristics, light weight, small size, and low cost. However, errors in IMU data and conventional navigation processes can lead to navigation errors. There errors can accumulate exponentially over time.

A zero-velocity update (ZUPT)-aided navigation method is one mechanism that can be used for pedestrian inertial navigation. A ZUPT-aided navigation method takes advantage of the semi-stationary state of a foot during the stance phase. Existing ZUPT systems often use fixed parameters that may result in errors for different users. In addition, existing ZUPT systems may not account for varying situations such as walking or running on different floor types and at different speeds. As such, these systems may have limitations for navigation scenarios. There is a desire for improvements in detecting varying pedestrian navigation scenarios and dynamically adapting the ZUPT-aided inertial navigation method parameters.

In addition, during pedestrian navigation, the foot is rarely truly stationary, even in the stance phase. The amount of residual motion in the foot during the stance phase and the corresponding uncertainty can vary under different navigation scenarios including differing floor types, such as hills, stairs, sand, grass, concrete, or combinations of these. Current pedestrian inertial navigation systems select ZUPT-aided inertial navigation method parameters without consideration of floor type. Furthermore, current floor type detection systems are primarily designed for vacuum cleaner systems, requiring additional sensors, and are not well-suited to pedestrian navigation conditions. While conventional floor type detection used for vacuum cleaners may be based on pressure sensors, ultrasonic transducers, and motor power monitors, these systems do not function with pedestrian navigation.

There is a desire for pedestrian navigation systems capable of detecting floor type without additional sensors and updating inertial navigation method parameters based on the detected floor type.

BRIEF SUMMARY OF THE EMBODIMENTS

Disclosed and claimed herein are systems and methods for inertial navigation accounting for varying navigation scenarios, including different gait frequencies and floor types.

In one embodiment, a method for pedestrian inertial navigation includes receiving, by a processor, inertial data from an inertial measurement unit, and partitioning, by the processor, the inertial data into a plurality of partitions. The method also includes reducing, by the processor, dimensionality of the plurality of partitions using principle component analysis and identifying, by the processor, a floor type of each partition. The method also includes adapting, by the processor, one or more inertial navigation parameters for each partition using identified floor type. The method also includes estimating, by the processor, a navigation position of the inertial measurement unit based on adapted inertial navigation parameters.

In one embodiment, the inertial data includes gyroscope data for a plurality of axes generated by the inertial measurement unit, and wherein the inertial measurement unit is mounted to a forefoot of a user.

In one embodiment, partitioning of the inertial data is based on at least one identified toe-off, each toe-off identified in the inertial data by identifying a peak in the inertial data.

In one embodiment, partitioning the inertial data includes partitioning based on at least one identified heel strike in the inertial data, each heel strike identified based on a peak in the inertial data.

In one embodiment, the method also includes determining a gait frequency based on a period of time between heel strikes, adapting a zero-velocity update threshold based on the gait frequency, and wherein estimating the navigation position is based on the adapted zero-velocity update threshold.

In one embodiment, the at least one heel strike is identified to determine a stance phase.

In one embodiment, reducing dimensionality includes generating an independent linear function for inertial data received from the IMU and using a validation approach to determine an output dimension of the principle component analysis.

In one embodiment, identifying a floor type includes using an artificial neural network trained by backpropagation with mini-batch gradient to identify at least one floor type based on floor hardness, motion of a foot, gait pattern and foot stability.

In one embodiment, adapting the one or more inertial navigation parameters includes modifying a navigation parameter using at least one of a velocity during a stance phase, an uncertainty corresponding to the velocity, and a zero-velocity update threshold.

In one embodiment, estimating a navigation position of the inertial measurement unit based on adapted inertial navigation parameters includes determining a navigation path relative to a starting point, wherein position measurements of the IMU are adapted to determine position of a user, wherein estimating the navigation position is based on the adapted zero-velocity update threshold.

In one embodiment, the method includes maintaining a zero-velocity update threshold while inertial data is below a threshold, and reducing the threshold in response to the inertial data exceeding the threshold.

Another embodiment is directed to a device configured for pedestrian inertial navigation. The device includes an inertial measurement unit configured to generate inertial data and a processor coupled to the inertial measurement unit. The processor is configured to receive inertial data from an inertial measurement unit, partition the inertial data into a plurality of partitions, and reduce dimensionality of the plurality of partitions using principle component analysis. The processor is also configured to identify a floor type of each partition, adapt one or more inertial navigation parameters for each partition using identified floor type, and estimate a navigation position of the inertial measurement unit based on adapted inertial navigation parameters.

In one embodiment, the inertial data includes gyroscope data for a plurality of axes generated by the inertial measurement unit, and wherein the inertial measurement unit is mounted to a forefoot of a user.

In one embodiment, partitioning of the inertial data is based on at least one of an identified toe-off and an identified heel strike.

In one embodiment, the processor is further configured to determine a gait frequency based on a period of time between heel strikes, and adapt a zero-velocity update threshold based on the gait frequency.

In one embodiment, reducing dimensionality includes generating an independent linear function for inertial data received from the IMU and using a validation approach to determine an output dimension of the principle component analysis.

In one embodiment, identifying a floor type includes using an artificial neural network trained by backpropagation with mini-batch gradient to identify at least one floor type based on floor hardness, motion of a foot, gait pattern and foot stability.

In one embodiment, adapting the one or more inertial navigation parameters includes modifying a navigation parameter using at least one of a velocity during a stance phase, an uncertainty corresponding to the velocity, and a zero-velocity update threshold.

In one embodiment, estimating a navigation position of the inertial measurement unit based on adapted inertial navigation parameters includes determining a navigation path relative to a starting point using, wherein position measurements of the IMU are adapted to determine position of a user.

In one embodiment, the processor is further configured to maintain a zero-velocity update threshold while the inertial data is below the threshold, and reduce the threshold in response to the inertial data exceeding the threshold.

Other aspects, features, and techniques will be apparent to one skilled in the relevant art in view of the following detailed description of the embodiments.

BRIEF DESCRIPTION OF THE DRAWINGS

The features, objects, and advantages of the present disclosure will become more apparent from the detailed description set forth below when taken in conjunction with the drawings in which like reference characters identify correspondingly throughout and wherein.

DETAILED DESCRIPTION OF THE EXEMPLARY EMBODIMENTS

Overview and Terminology

Figure 1:
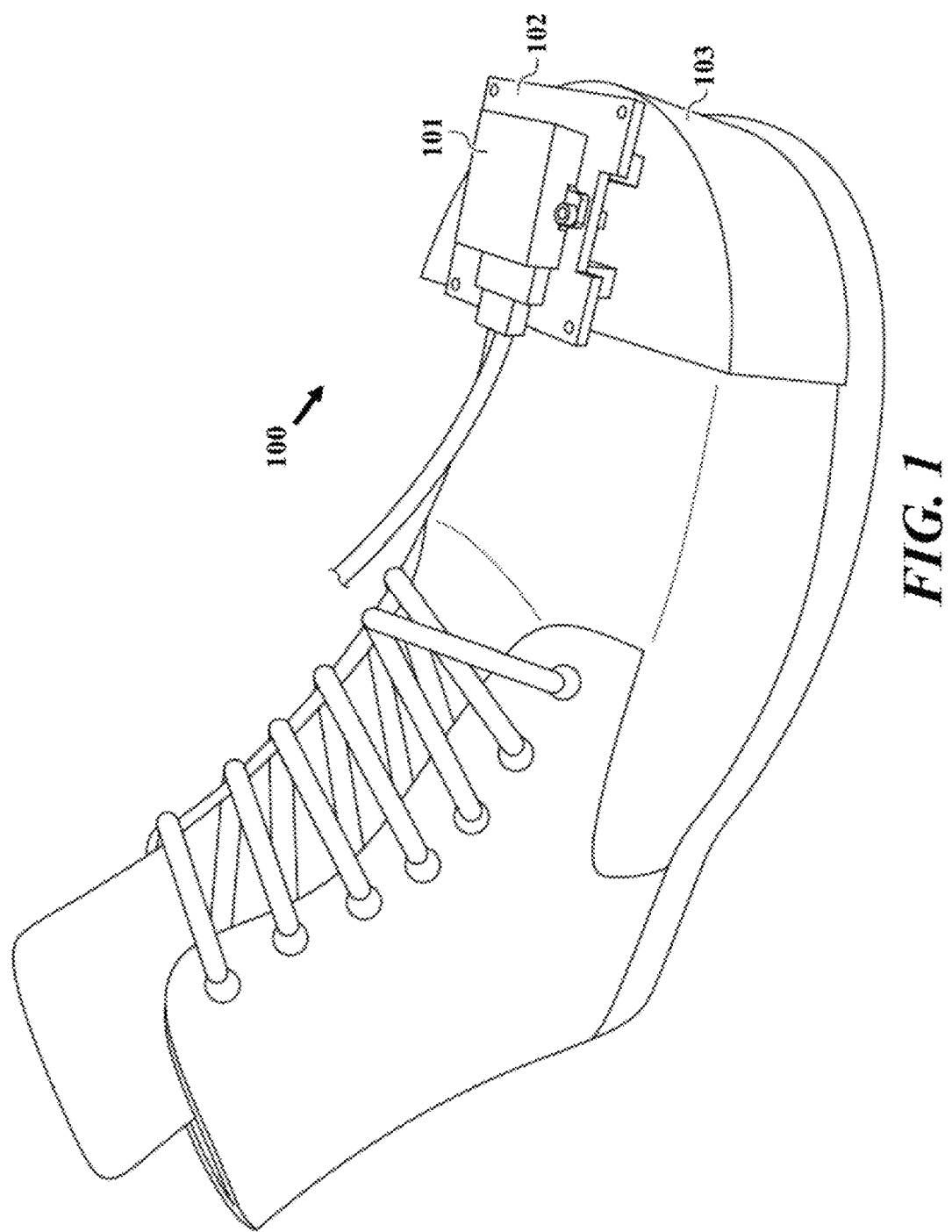
FIG. 1 illustrates a measurement configuration including an inertial measurement unit according to one or more embodiments.

In pedestrian inertial navigation, the navigation system may be used under various navigation scenarios. For example, the user may move with different patterns: walking, running, jumping, and even crawling. The user may move on different types of floors: going upstairs, going downstairs, going uphill, and going downhill. The user may even navigate on floors or ground surfaces of different materials, such as concrete, sand, grass, or surfaces people may walk on in general. Different paces of motion will also lead to changes in the human gait dynamics. All these different factors may affect the parameters to be used in the zero-velocity update (ZUPT)-aided pedestrian inertial navigation algorithm, such as the threshold used for the stance phase detection, the residual velocity of the foot during the stance phase, and the corresponding measurement uncertainty. In order to improve navigation accuracy in different navigation scenarios, the inertial navigation parameters should be adjusted accordingly, i.e., the inertial navigation algorithm should be able to adapt to different navigation scenarios.

Pedestrian inertial navigation has been of great interest in recent years for human health monitoring, personal indoor navigation, and localization systems for first responders. To enable such applications with MEMS-based IMUs, error-suppressing methods are needed to compensate for IMU errors. One error-suppressing method is the Zero-velocity Update (ZUPT)-aided pedestrian inertial navigation, where a semi-stationary state of the foot during the stance phase is utilized to limit the propagation of navigation errors.

In the ZUPT-aided pedestrian inertial navigation, however, many inertial navigation parameters need to be properly selected, such as velocity of the foot during the stance phase, the corresponding uncertainty, and the ZUPT detection threshold. All these inertial navigation parameters are related to the floor type on which the user walks. Embodiments may use a Multiple Model (MM) approach to achieve the adaptive selection of these inertial navigation parameters where the floor type is first identified into different models, and then appropriate inertial navigation parameters are assigned accordingly.

Due to the complicated dynamics of the foot during navigation, many methods may be used to adapt the navigation system to various navigation scenarios. For example, adaptive stance phase detection may be used to adapt the system to various gait paces. Machine-Learning may also be used to conduct Human Activity Recognition (HAR) for inertial sensor calibration and Multiple Model estimation. Floor type is an important factor to be determined.

In one embodiment, a method for pedestrian inertial navigation is provided that utilizes one or more stance phase components. Walking may generally be characterized as having a stance phase component, wherein a foot is in contact with a ground surface, and a swing phase component, wherein the foot is not in contact with the ground surface. A stance phase as used herein may relate to a period where a foot is on the ground and can include one or more of a heel strike, early flatfoot, late flatfoot and tow off. A stance phase may relate to non-swing phase of a foot during walking. According to embodiments, inertial data is received from an inertial measurement unit to characterize foot motion and as a result provide information about a user's movements. According to embodiments, one or more characteristics or events of a stance phase may be determined from received inertial measurement data. By way of example, embodiments may include identifying a toe-off in the inertial data. Toe-off may be when toes of a foot leave the ground and thus the start of a swing phase (swing of the foot. According to other embodiments, a heel strike may be identified. A heel strike may be the start of a stance phase, when a heel touches a ground surface or floor. Although embodiments refer to walking, it should be appreciated that the principles of disclosure may be used to characterize human movement for one or more types of motion, including jogging, running, lateral motion, ascending/descending stairs, etc.

According to embodiments, inertial measurement data may be provided by at least one inertial measurement unit worn by a user, such as on a user's foot, user shoe, etc. Using one or more stance elements, such as toe-off and heal strike, inertial data may be partitioned into multiple partitions. Processes described herein can reducing dimensionality of received data using principle component analysis (PCA), and can identify a floor type of each partition. The method further includes adapting one or more inertial navigation parameters using a multiple model Kalman filter and the identified floor type and estimating a navigation position based on the adapted one or more inertial navigation parameters.

In one embodiment, the inertial data includes gyroscope data and identifying a toe-off in the inertial data includes identifying a peak in the gyroscope data, and partitioning the inertial data includes partitioning the data based on the identified toe-off. According to another embodiment, the one or more inertial navigation parameters includes one or more of a velocity during a stance phase, an uncertainty corresponding to the velocity, and a zero-velocity update threshold.

In another embodiment, a method for pedestrian inertial navigation includes receiving inertial data from an inertial measurement unit, and identifying heel strikes in the inertial data based on a peak in the inertial data. The method further includes determining gait frequency based on a magnitude of the peak in the inertial data, adapting a zero-velocity update threshold based on the gait frequency, and estimating a navigation position based on the adapted zero-velocity update threshold. In one embodiment, the method further includes holding the zero-velocity update threshold during detection of a stance phase in the inertial data, in order to take advantage of the whole stance phase period, and reducing the threshold in response to the inertial data exceeding the threshold.

Embodiments, provide systems, device configurations and methods to conduct the floor type detection during human walking based on IMU data. A foot-mounted IMU is used in the described embodiments. FIG. 1 illustrates an example of a foot-mounted IMU, which reduces the complexity of the overall system. The floor type detection result is then used in the ZUPT-aided pedestrian inertial navigation in the Multiple Model approach. Navigation accuracy is improved through the use of floor type detection. In one embodiment, the inertial measurement unit is attached to a toe portion of a user's foot.

Figure 5:
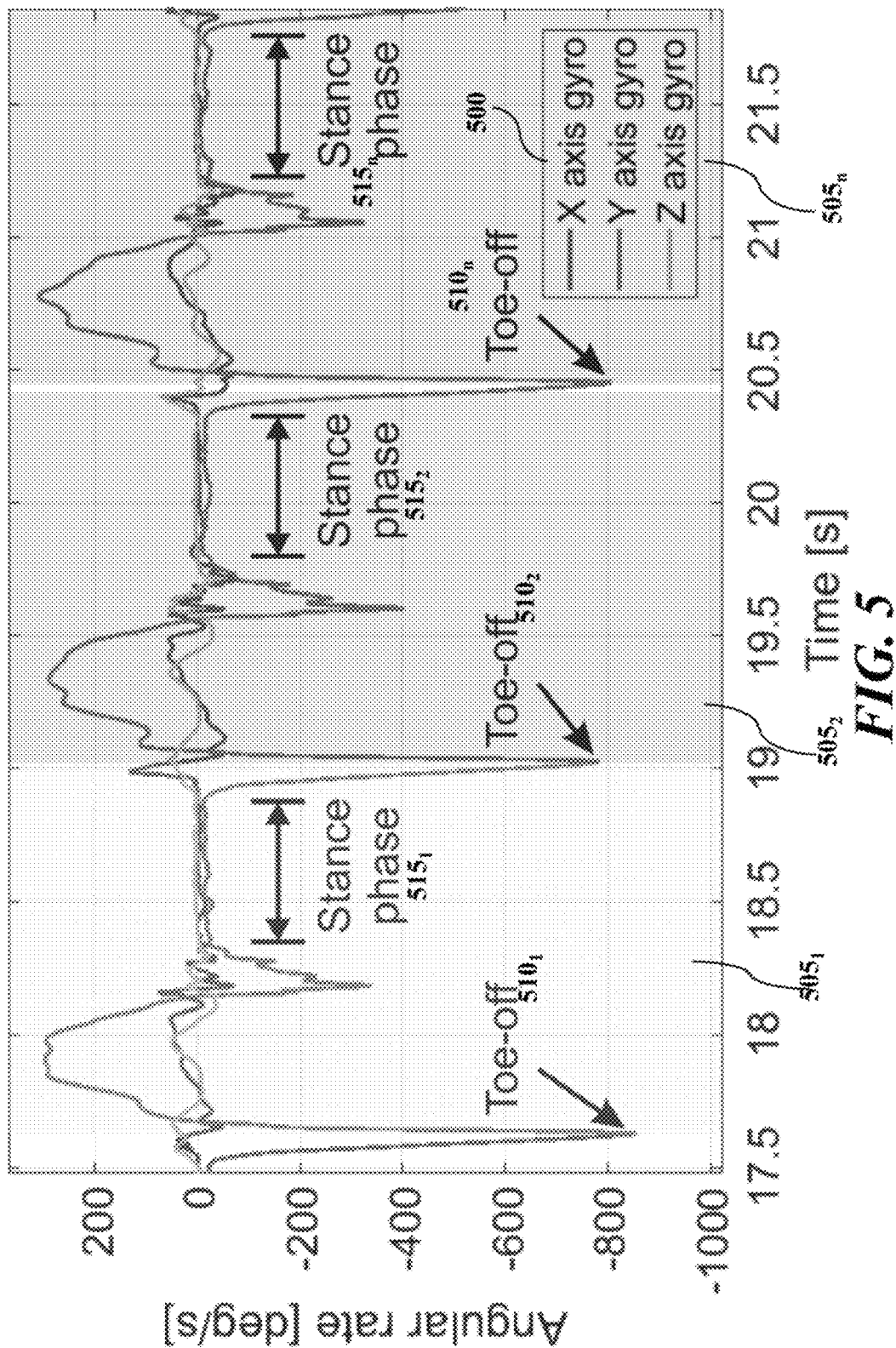
FIG. 5 illustrates IMU data partitioning based on toe-off detection according to one or more embodiments.

FIG. 1 illustrates measurement configuration 100 including inertial measurement unit 101 attached to the foot of a user according to one or more embodiments. According to one embodiment, an IMU 101 is rigidly mounted above the forefoot. IMU 101 may be configured to detect movement of a user foot and output data for one or more planes of movement. According to embodiments, IMU 101 includes a plurality of accelerometers. IMU 101 may output data to a processor by one or more of a wired and wireless connection. According to embodiments, IMU 101 may be configured with a sampling rate of 400 Hz. According to embodiments, IMU 101 may be configured to output accelerometer and gyroscopic data for each of an X axis, Y axis, and Z axis. Exemplary data for IMU 101 is shown in FIG. 5.

According to embodiments, IMU 101 is rigidly mounted above the forefoot of a shoe (i.e., boot) by support structures shown as platform 102 and toe cap 103. Platform 102 and toe cap 103 may be three-dimensional-printed fixtures. According to embodiments, measurement configuration 100 improves navigation accuracy using the toe mounted mounting configuration. Other mounting locations may be used, including under the toe, or any location between the heel and toe, or embedded in footwear. Different mounting positions of IMU 101 may lead to different correlation relations between the shock level and the gait frequency. Measurement configuration 100 and IMU 101 may be used in one or more configurations described herein.

Floor Type Detection

Figure 2:
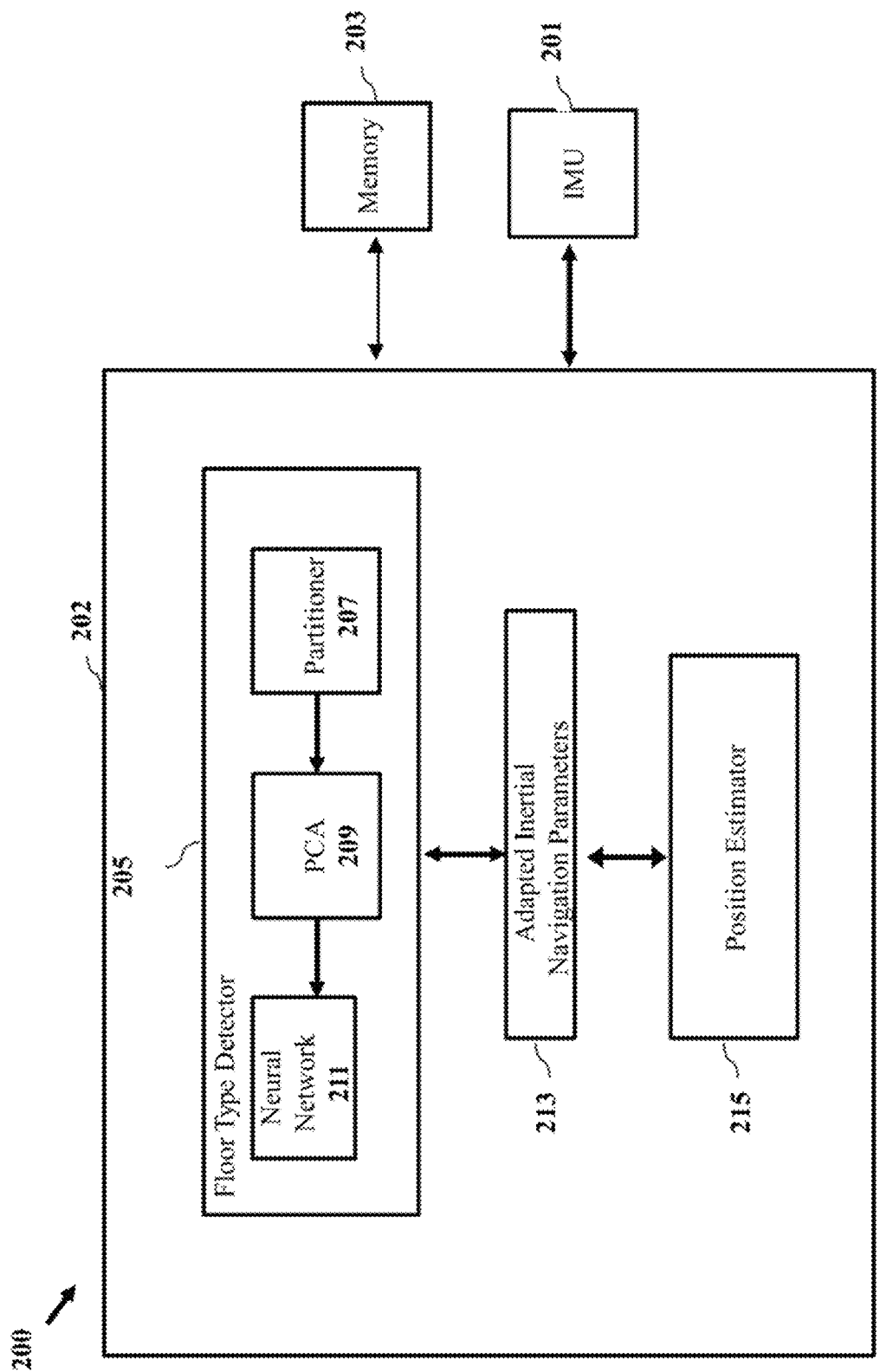
FIG. 2 illustrates a pedestrian inertial navigation system including a floor type detector according to one or more embodiments.

FIG. 2 illustrates an embodiment of an adaptive threshold aided pedestrian inertial navigation system 200. The inertial navigation system 200 includes a processor 202 and an inertial measurement unit (IMU) 201 that provides data used for navigation position estimates. According to embodiments, processor 202 may be part of a device, such as wearable device (e.g., smart watch, etc.), or a portable device (e.g., mobile phone, handle device, etc.). The IMU 201 may include one or more accelerometers, gyroscopes or other inertial measurement sensors. As described herein, IMU 201 may be mounted to a pedestrian or wearer's foot, such as the toe portion of a shoe. Data from IMU 201 and data used and produced in the navigation position estimation by processor 202 may be stored in memory 203. Memory 203 may be a computer readable storage device. Processor 202 is configured to perform one or more determinations and functions, shown as blocks in FIG. 2. By way of example, processor 202 may be configured to perform a plurality of functions including functions for a floor type detector 205, adapted inertial navigation parameters 213 and position estimator 215. The floor type detector functions 205 may include a partitioner 207 configured to partition the inertial data based on gait cycle, a principle component analysis (PCA) unit 209 configured to reduce dimensionality of the partitioned inertial data, and a neural network 211 configured to detect the floor type for each partition. Inertial navigation parameters are adapted at block 213 to the identified floor type and may be stored in the memory 203 or other computer readable medium. The position estimator functions at block 215 may use the adapted inertial navigation parameters 213 to estimate the current navigation position.

Figure 3:
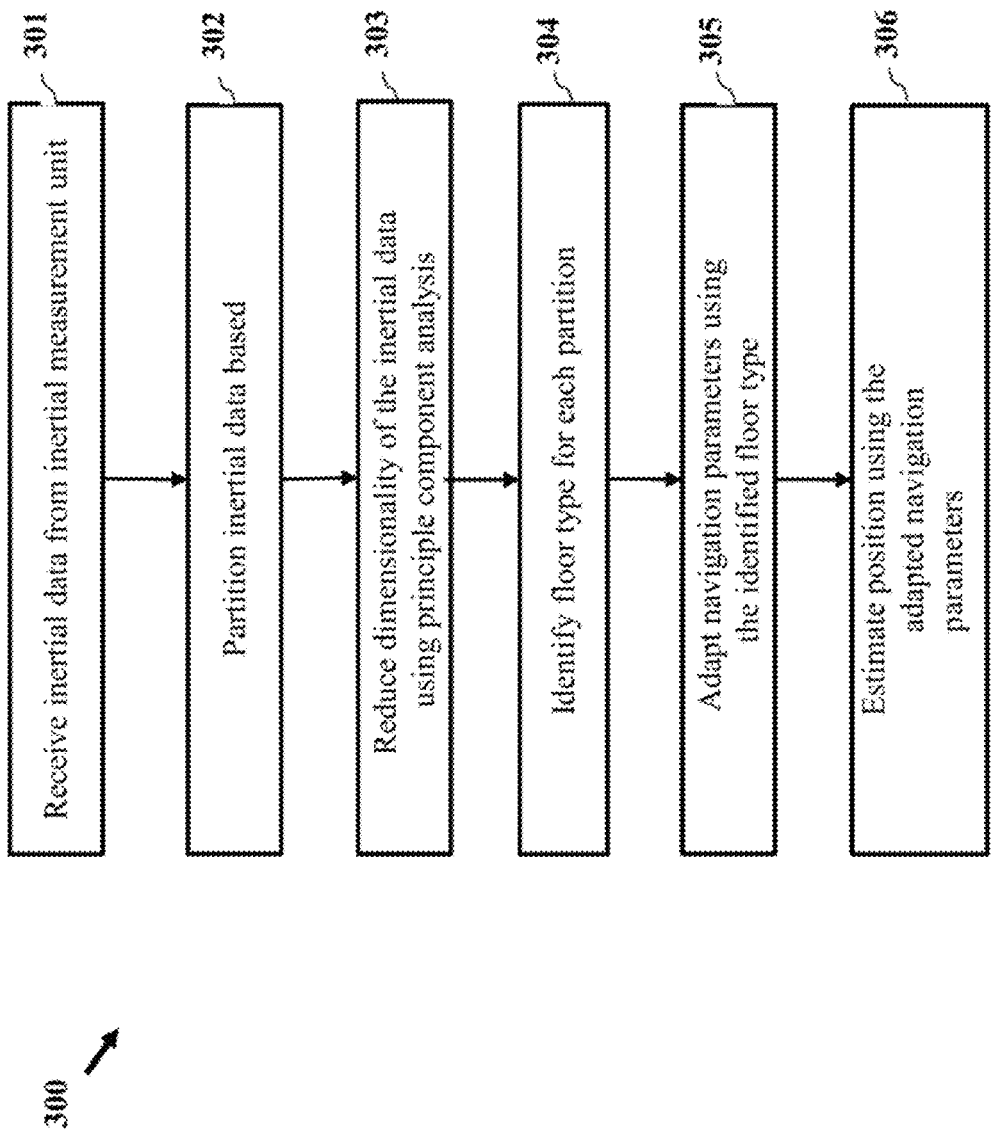
FIG. 3 illustrates a process for navigation using floor type identification according to one or more embodiments.

One or more embodiments are provided to identify floor types in pedestrian inertial navigation and for adaptive estimation of navigation states under various navigation scenarios. FIG. 3 illustrates process 300 for navigation using floor type identification. Process 300 may be performed by a processor (e.g., processor 202). Process 300 may be initiated by receiving inertial measurement data from an IMU (e.g., IMU 101, IMU 201, etc.) at block 301. Inertial data received at block 301 may include gyroscope data for a plurality of axes generated by an IMU. The IMU may be mounted to a forefoot of a user. Data of inertial measurement unit (IMU) may be partitioned at block 302 into a plurality of partitions. Partitioning of the inertial data may be based on at least one identified toe-off, each toe-off identified in the inertial data by identifying a peak in the inertial data. As will be discussed with reference to FIG. 16, partitioning may be based on a heel strike according to other embodiments. According to embodiments, each partition may be performed to correspond, at least roughly, to a full human gait cycle. The partition of inertial data may be based on toe-off peak. According to other embodiments and as described below with reference to FIG. 16, data may be partitioned based on at least one identified heel strike.

Process 300 may include performing a Principal Component Analysis (PCA) on each partition to reduce dimensionality of the data at block 303. Reducing dimensionality can include generating an independent linear function for inertial data received from the IMU and using a validation approach to determine an output dimension of the principle component analysis. At block 304, a floor type may be identified for each partition. According to one embodiment, floor type may be identified at block 304 using IMU data and an artificial neural network configured for the floor type identification. Floor type identification can include using an artificial neural network trained by backpropagation with mini-batch gradient to identify at least one floor type based on floor hardness, motion of a foot, gait pattern and foot stability. The identification result may be used to adapt inertial navigation parameters at block 305. Updating at block 305 may be based on a Zero-Velocity-Update (ZUPT)-aided pedestrian inertial navigation in a Multiple Model (MM) approach. A processor may adapt, or update, one or more inertial navigation parameters for each partition using identified floor type. According to embodiments, adapting the one or more inertial navigation parameters includes modifying a navigation parameter using at least one of a velocity during a stance phase; an uncertainty corresponding to the velocity; and a zero-velocity update threshold. Updating at block 305 may include maintaining a zero-velocity update threshold while inertial data is below a threshold, and reducing the threshold in response to the inertial data exceeding the threshold.

The navigation position of an inertial measurement unit, and that of a user of the inertial measurement unit, may be estimated using the adapted inertial navigation parameters at block 306. Estimating a navigation position of the inertial measurement unit based on adapted inertial navigation parameters can include determining a navigation path relative to a starting point using, wherein position measurements of the IMU are adapted to determine position of a user, wherein estimating the navigation position is based on the adapted zero-velocity update threshold. By way of example, methods described in this disclosure identify at least five navigation scenarios or different floor types: walking on hard floor, walking on grass, walking on sand, walking upstairs, and walking downstairs. It should be appreciated that other floor types or navigation scenarios may be identified using the principles and teachings described in this application. The disclosed methods result in reduced navigation error under dynamically changing navigation scenarios.

Figure 4:
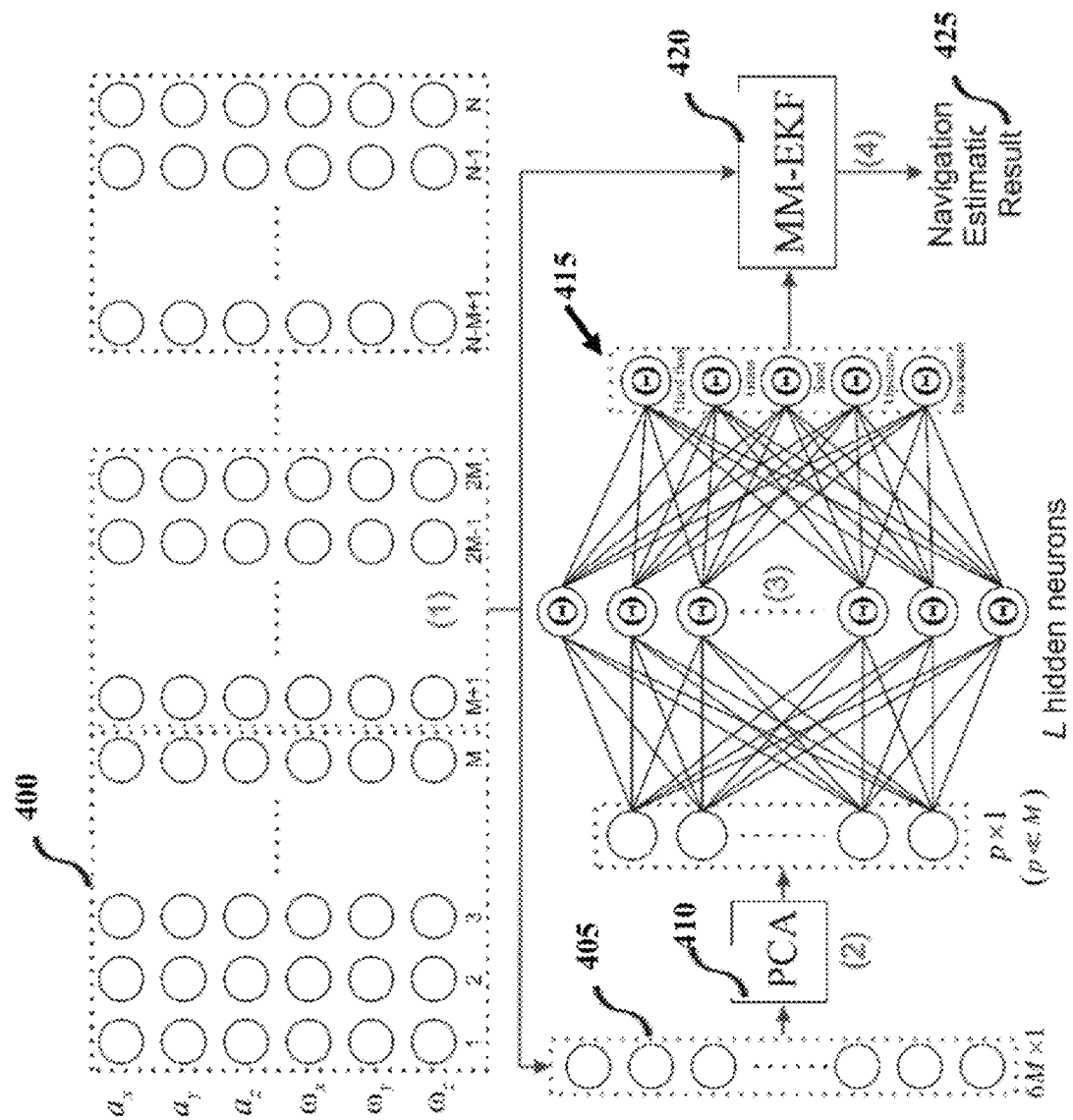
FIG. 4 illustrates a graphical representation of navigation estimation according to one or more embodiments.

FIG. 4 illustrates a graphical representation of navigation estimation. According to embodiments, navigation estimation may base based on a plurality of IMU data points or measurements, shown as IMU data 400. According to embodiments, IMU data is partitioned, principle component analysis (PCA) is performed, floor type may be identified and a multiple mode extended Kalman filter may be used to estimate a navigation result, such as a position, position estimate, and range measurement. FIG. 4 illustrates dividing IMU data 405 into different partitions of length M, with each partition roughly corresponding to a full gait cycle. According to embodiments, length of each partition is fixed, so that they are of the same dimension to facilitate the following steps. According to embodiments, floor identification may be performed on each partition, such as partition 405 of IMU data 400. Second, Principal Component Analysis (PCA) is conducted at block 410 on the input data to reduce dimensionality from 6M to p. The value p can be selected by considering a trade-off between the identification accuracy and the computational load: more dimensionality reduction by the PCA leads to a simpler learning step at the cost of lower identification accuracy. Third, a two-layer artificial neural network 415 is trained to conduct the floor type identification. The number of nodes or neurons in the hidden layer L may be selected with consideration of another trade-off between accuracy and computational load. Fourth, the floor type identification result is used in a Multiple Model Extended Kalman Filter (MM-EKF) 420 for the ZUPT-aided pedestrian inertial navigation at 425.

Implementation

A. Data Partition

FIG. 5 illustrates IMU data partitioning based on toe-off detection according to one or more embodiments. IMU data 500 is received for one or more axes, such as gyroscopic data for each of an X axis, Y axis, and Z axis. According to one embodiment, IMU data may be first partitioned into different gait cycles as shown in FIG. 5 as $505_{1-n}$. One of the most recognizable features in the IMU data is the y-axis gyroscope peak during the toe-off of the foot $510_{1-n}$, which was used as the start mark of each partition according to one embodiment. According to an exemplary illustration, the gait frequency in the example of FIG. 5 is approximately 90 steps per minute and the IMU sampling rate is 400 Hz, so length of each partition was set to a fixed value (e.g., 533). The actual length of each gait can vary. For example, there is a gap between the second and third data partitions $505_2$ and $505_n$ in FIG. 5 indicating that the second partition $505_2$ ends before the third partition $505_n$ begins. The method described in this application will function properly even if each partition does not necessarily end at the following toe-off event. FIG. 5 also illustrates a stance phases $515_{1-n}$ for each data partition $505_{1-n}$. One or more of partitions $505_{1-n}$, toe-off $510_{1-n}$, and stance phase $515_{1-n}$ may be used for floor type detection and position estimation.

B. Principal Component Analysis

According to embodiments, IMU data at each time step can include 6 data measurements, including 3 from accelerometer data and 3 from gyroscope data. In this non-limiting example, the dimensionality of each partition was 533×6=3198, which would lead to large amount of computation in the following training of the neural network, if no dimensionality reduction was conducted. Therefore, principle component analysis (PCA) is used to reduce the dimensionality of data before the subsequent learning steps according to embodiments. The basic idea of the PCA (e.g., PCA) is to find new variables, or principal components, by way of feature selection and/or feature extraction. PCA as discussed herein may generate an independent linear function for the original dataset and successively maximize the variance. By way of example an independent linear function may be generated for inertial data received from an IMU. It can be shown that the PCA can be accomplished by solving an eigenvalue/eigenvector problem. In this non-limiting example, 1673 partitions may be collected and labeled with the corresponding floor types: walking on hard floor, walking on grass, walking on sand, walking upstairs, and walking downstairs. The corresponding eigenvalues of the centered data matrix after conducting the Singular Value Decomposition (SVD) are distributed continuously, making obtaining a threshold by observation difficult. Therefore, a validation approach may be used to determine an acceptable output dimension of the PCA.

C. Artificial Neural Network

After conducting the PCA to reduce dimensionality, a two-layer artificial neural network may be trained and used for the floor type identification. A backpropagation method with mini-batch gradient descent may be used to train the weights in the artificial neural network. However, the number of nodes in the hidden layer L can be adjusted for performance vs complexity and should be determined before training the neural network.

Two design parameters may be tuned in the design of the pedestrian inertial navigation system: the dimensionality of the PCA output p, and the number of hidden nodes L. Both p an L have an effect on the complexity and accuracy of the method. A validation method may be used to determine appropriate values for the two design parameters. In this non-limiting example, 20% of training data are randomly selected and reserved as an independent validation set to evaluate the training effects. The remaining 80% of data are utilized to train the neural network. In this non-limiting example, the weights of the artificial neural network are selected to be those that achieved highest identification accuracy over the validation set.

Figure 6:
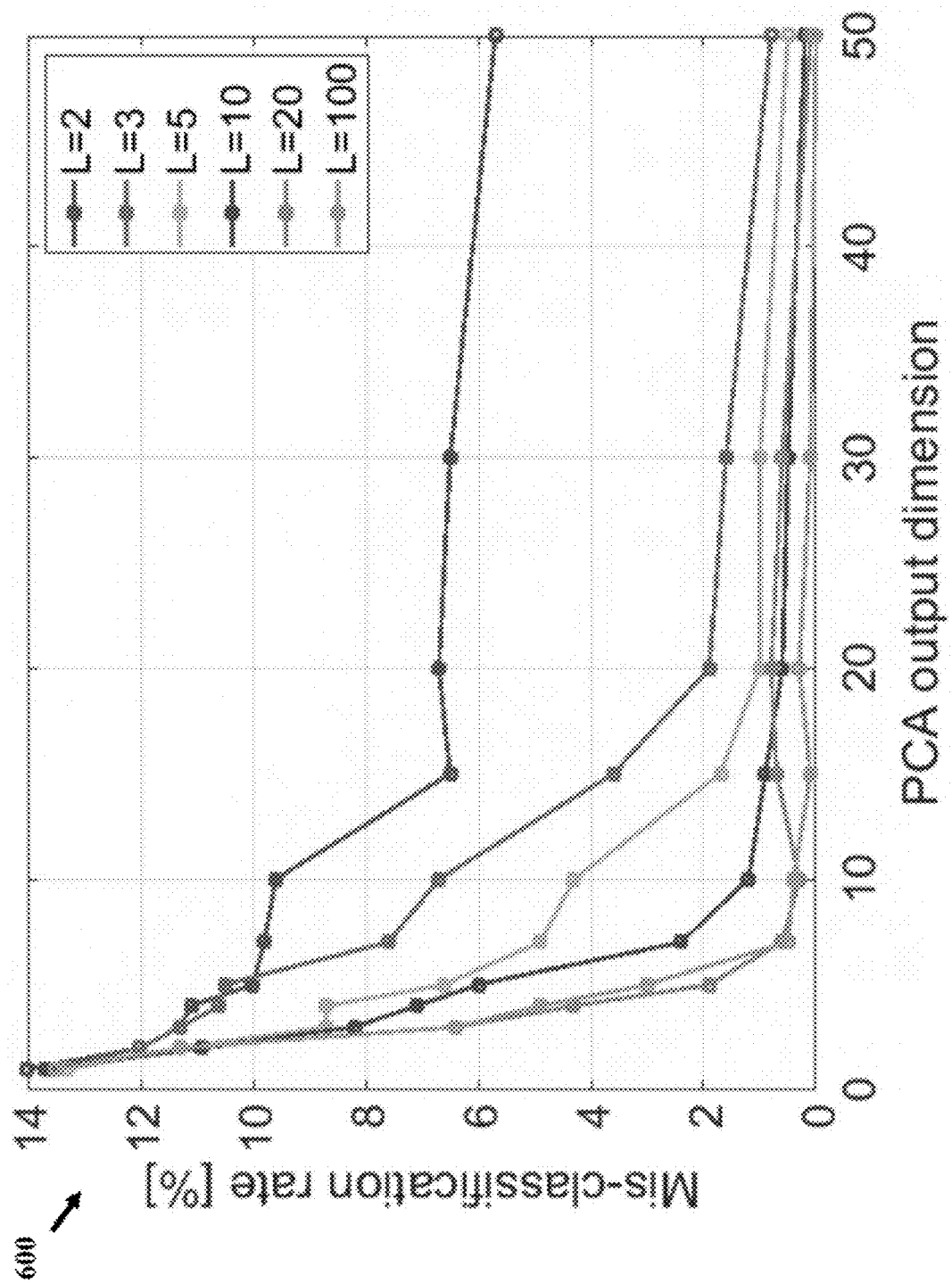
FIG. 6 illustrates relationships between principle component analysis (PCA) output dimensions, the number of nodes in the neural network, and misclassification rate for floor type detection according to one or more embodiments.

FIG. 6 illustrates changes in the misclassification rate 600 according to embodiments over the entire available data, that result from selecting different values for p and L. The x-axis represents the PCA output dimension, and the y-axis represents the misclassification rate. Different lines show the results with different numbers of nodes in the hidden layer of the neural network. Generally, higher PCA output dimension p and larger number of nodes in the hidden layer improve accuracy. In this non-limiting example, if only 2 nodes are used in the hidden layer, the misclassification rate remains higher than 5% regardless of the PCA output dimension. However, if the number of hidden nodes is increased to 3, the misclassification rate is reduced to around 1% with PCA output dimension of over 50. When the number of hidden nodes is greater than 20, the improvement in the misclassification rate due to increasing number of nodes is only marginal. In the non-limiting illustrative example, the parameter L is selected to be 20.

The PCA output dimension p also affects the accuracy of classification.

Figure 7:
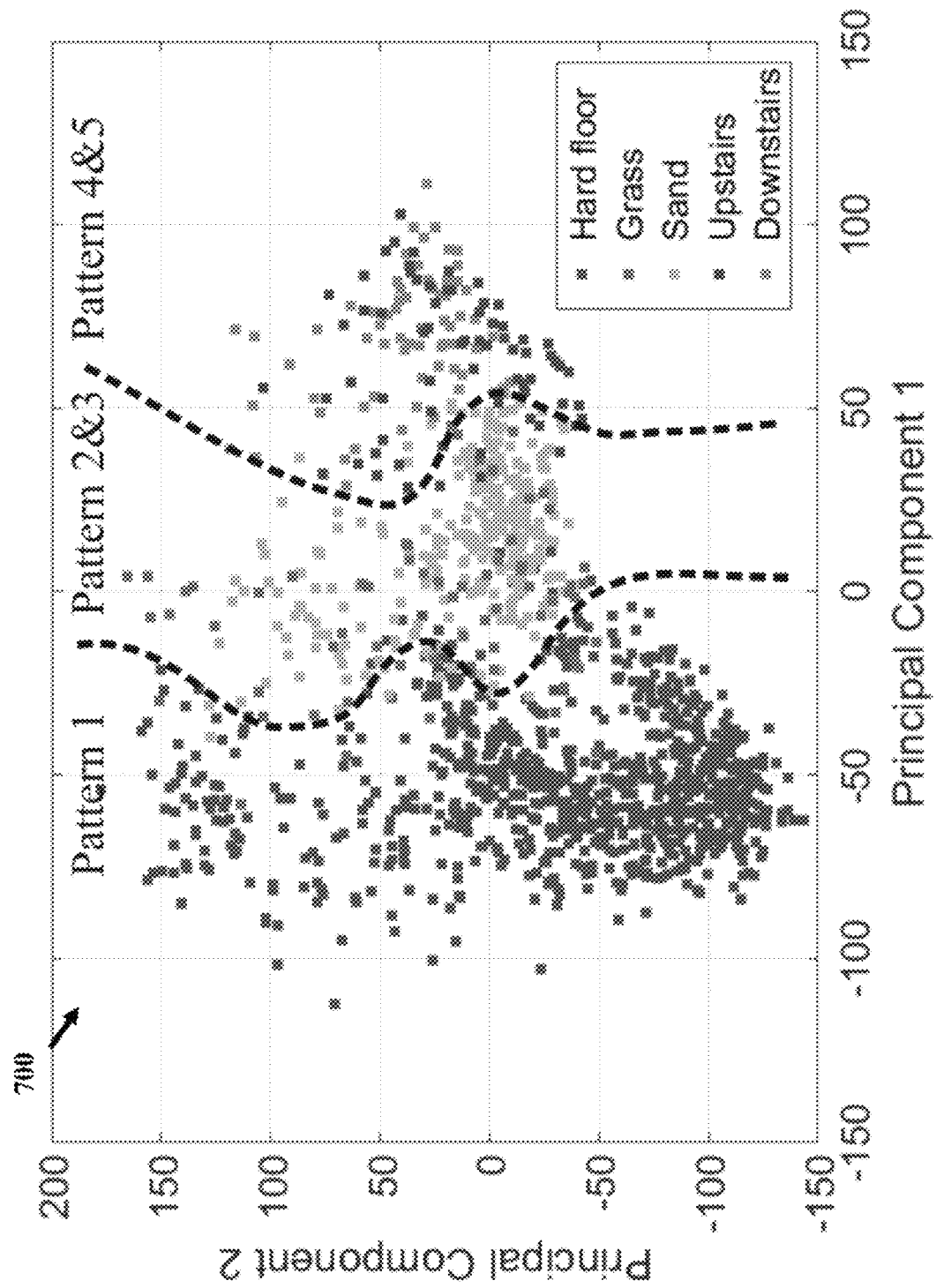
FIG. 7 illustrates a graphical representation of principle component analysis according to one or more embodiments.

FIG. 7 illustrates a graphical representation of principle component analysis, including various patterns identifiable based on two principle component dimensions, p=2, according to one or more embodiments. As illustrated, with just two principle component dimensions, a pattern corresponding to walking on a hard floor can be identified and separated from other patterns. The patterns for walking on grass and sand are mixed together, but distinguishable from pattern for walking on a hard floor and the patterns for walking up and down stairs. Some confusion between sand and grass and between upstairs and downstairs is possible with a PCA output dimension of p=2. As described and shown in FIG. 8, considerable improvement is possible with a PCA output dimension of p=3 or greater shown as 805, and very high accuracy is possible with p=10, shown as 810.

Figure 8:
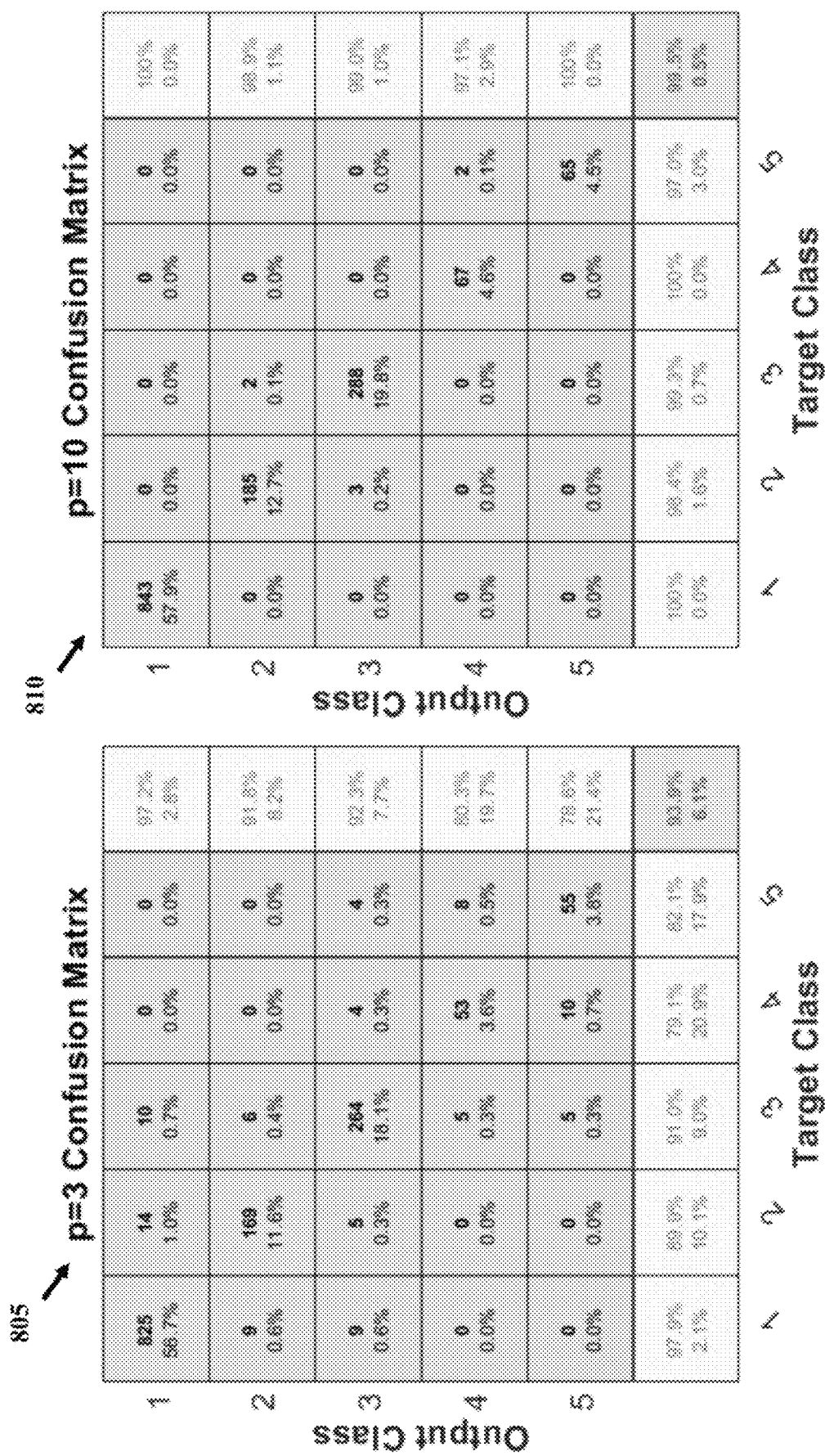
FIG. 8 illustrates confusion matrices for floor type identification according to PCA output dimensions of 3 and 10 according to one or more embodiments.

FIG. 8 is a non-limiting illustration of the confusion matrices of the floor type identification results with the PCA output dimension of p=3 and p=10, respectively. A classification accuracy of 93.9% is demonstrated with p=3. The accuracy improves to 99.5% as p increases to 10, with only a few misclassifications occurring between walking on grass and walking on sand, and between walking upstairs and downstairs. The misclassifications can be explained with the following reasons:

The floor is soft for the case of sand and grass, and the hardness of the floor may vary depending on the thickness of the sand or grass layer even within the same floor type.

The motion of the foot is more random when it is on the floor in the case of walking on sand and grass compared to the case of hard floor. Therefore, more outliers may occur and be misclassified.

The gait patterns of walking upstairs and downstairs are generally different from the case of walking on the flat surface. Therefore, it is less likely to misclassify between the first three classes and the last two.

The foot is less stable when walking on stairs due to a large magnitude of motion. Thus, it is possible to misclassify between walking on stairs and walking on sand, especially if the PCA output dimension p is small and much information is lost after applying PCA to the original data. In the case of p=10, shown as 810, high classification accuracy may be obtained even with dimensionality reduction of more than 300 times.

D. Multiple Model Extended Kalman Filter

Figure 9:
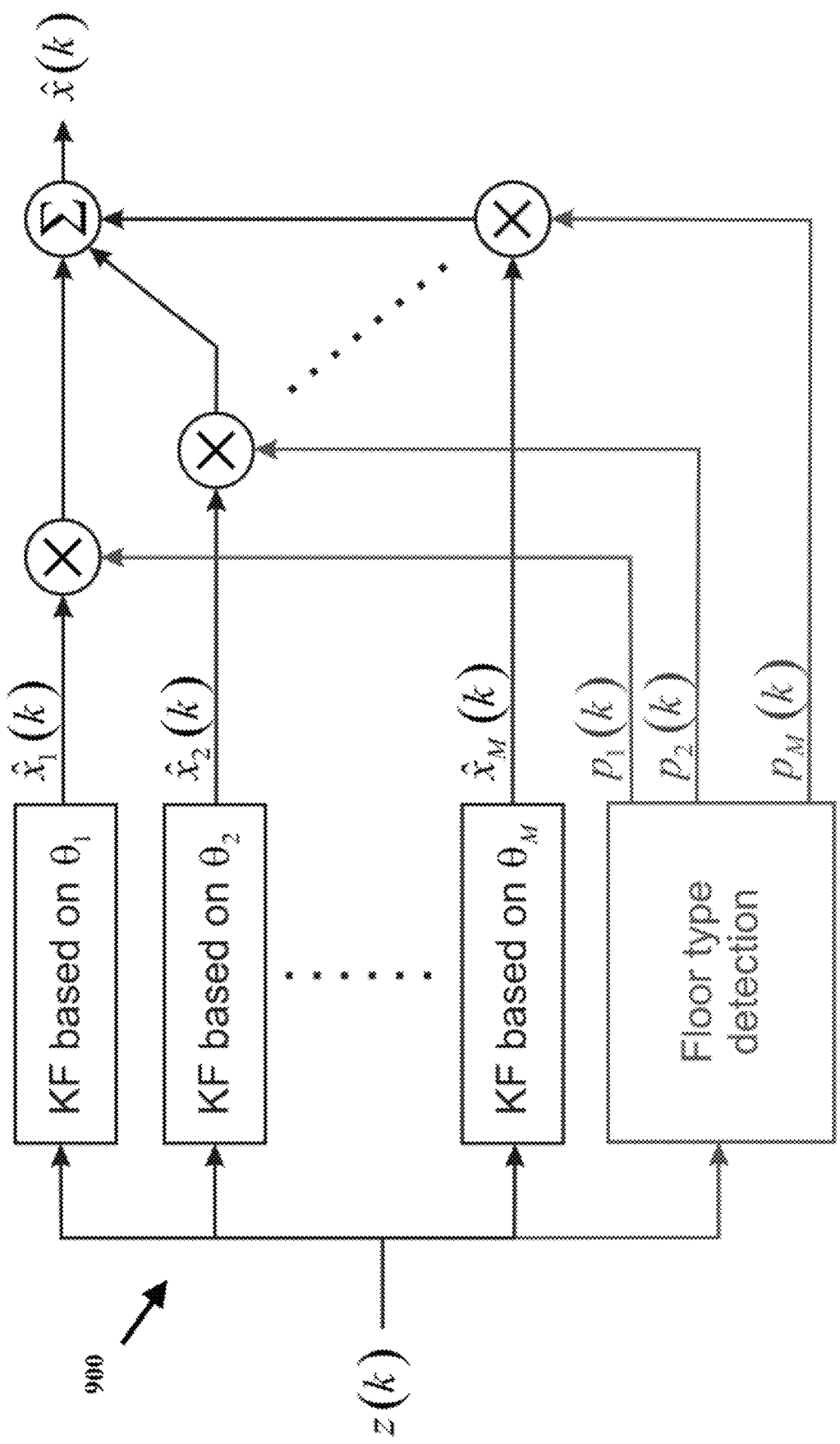
FIG. 9 illustrates how a multiple model Kalman filter is modified to include floor type detection to adapt inertial navigation parameters according to one or more embodiments.

A multiple model extended Kalman filter may be used to adapt the inertial navigation parameters to different floor types. In the standard multiple model Kalman filter approach, a set of parallel Kalman filters are involved, each representing a model with the different parameters. The Kalman filter provides both the estimated system state and the innovation, or the measurement residual, of the estimate. The innovations from all Kalman filters are input into a hypothesis test to calculate the probability of each model. The final estimation results are obtained by calculating the weighted average of the estimated results from all pairs. According to embodiments, instead of estimating the probability of each model based on hypothesis and the innovation of each Kalman filter, the floor type detection discussed previously is used. A schematic 900 of the multiple model Kalman filters with floor type identification is shown in FIG. 9.

The differences between each model include the threshold for ZUPT detection, the residual velocity during the stance phase, and the corresponding velocity uncertainty. Each of these inertial navigation parameters may be obtained by separate calibrations, and the details have been reported in Y. Wang, Y.-W. Lin, S. Askari, C.-S. Jao, and A. M. Shkel, "Compensation of Systematic Errors in ZUPT-Aided Pedestrian Inertial Navigation," IEEE/ION Position, Location and Navigation Symposium (PLANS), Apr. 20-23, 2020, Portland, OR, USA, and Y. Wang, S. Askari, A. M. Shkel, "Study on Mounting Position of IMU for Better Accuracy of ZUPT-Aided Pedestrian Inertial Navigation," IEEE International Symposium on Inertial Sensors and Systems (INERTIAL), Apr. 1-5, 2019, Naples, FL, USA.

Navigation Result

Figure 10:
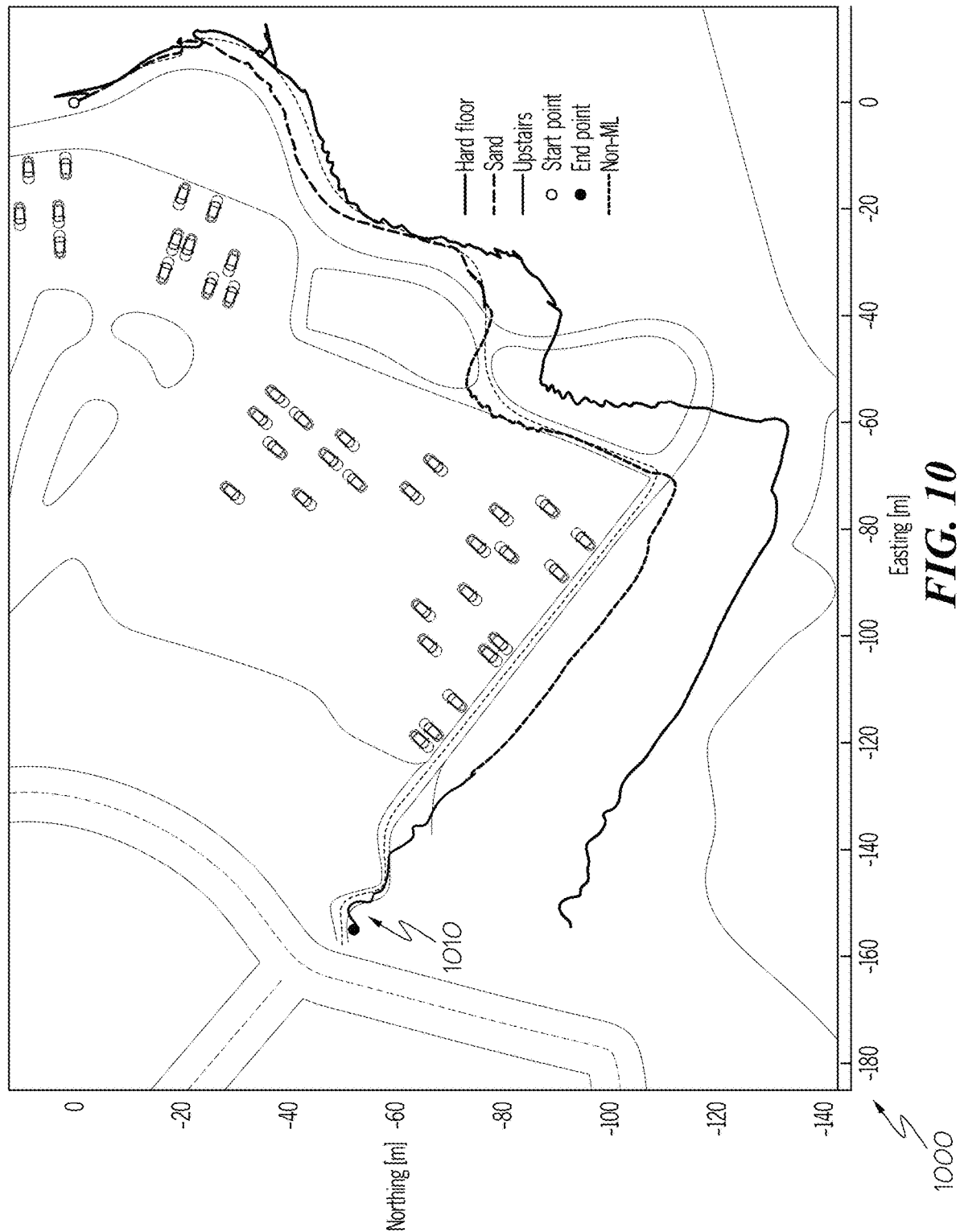
FIG. 10 illustrates a navigation path according to one or more embodiments compared to a ground truth navigation path.

In order to demonstrate the effect of the floor type identification, a navigation path 1000 including a starting point 1010 involving sand, hard floor, and stairs is illustrated in FIG. 10. The user first walked on the sand for about 2 minutes, then walked on the hard floor for another 2 minutes, and finally walked upstairs for about 1.5 minutes. The total length of the navigation path is about 320 m. The navigation results with and without the floor type identification are presented in FIG. 10. The dashed line is the ground truth, and the solid line is the estimated trajectory without the floor type detection. The estimated trajectory with the floor type detection is presented by three segments, corresponding to three different floor types identified by the method. The smaller final estimation error demonstrates the effects of the floor type detection on improving the accuracy of pedestrian inertial navigation.

In this application, we discussed methods of the floor type identification for pedestrian inertial navigation. A combination of the Principal Component Analysis and the artificial neural network was explored, achieving a high classification accuracy with a reasonable amount of calculation. Floor type identification accuracy of as high as 99.5% was obtained over the training set, and a reduction of the navigation error was demonstrated, verifying the effects of the floor type identification.

Adaptive Threshold for Zero-Velocity Detector

To implement a zero-velocity update (ZUPT)-aided navigation method, according to some embodiments, a zero-velocity detector is used to determine if the inertial measurement unit (IMU) is stationary by comparing test statistics to a zero-velocity update threshold. However, different gait patterns lead to different gait dynamics, and as a result, different zero-velocity update thresholds, or an adaptive threshold, are better suited for different navigation scenarios, such as running versus walking. A variety of threshold tuning methods are possible. One method involves tuning the threshold empirically in an ad-hoc manner. Another method involves adjusting inertial navigation method parameters based on the period of gait cycle (or equivalently, the walking speed) obtained by presetting the walking speed or Fourier transform. Sensor fusion techniques may also be used to tune the inertial navigation method parameters. Machine learning may be used to classify the motion first, and then assign the threshold accordingly. All these techniques approach threshold adjustments by either increasing complexity of the system, or making assumptions about gait speed. One or more embodiments of the disclosure are directed to providing an adaptive thresholds in ZUPT-aided navigation without adding hardware complexity and with less computational load on the system compared to machine learning approaches.

Zero-Velocity Detector

One or more embodiments are directed to processes and device configurations for zero-velocity detection. A zero-velocity detector can be mathematically expressed as a binary hypothesis testing problem, where the detector can choose between the two hypotheses: $H_0$ and $H_1$, where $H_0$ corresponds to the case where the IMU is moving, while $H_1$ corresponds to the case where the IMU is stationary. A common approach is to apply the Neyman-Pearson theorem and compare the likelihood ratio with some predefined threshold $\gamma$: choose $H_1$ if $$L(z_k) = \frac{p(z_k \mid H_1)}{p(z_k \mid H_0)} > \gamma \quad (1)$$

where $z_k = \{y_k\}_{k=n}^{n+N-1}$ is the N consecutive IMU data between time index n and n+N−1, and $L(\cdot)$ is the likelihood ratio of probability of the measurement.

A stance hypothesis optimal detector is one type of zero-velocity detector. This detector is based on assumptions that, during the stance phase, the magnitude of the specific force that the IMU is experiencing is equal to gravity, and the angular rate of the IMU is zero. Since the dynamics of human gait are complicated, if not unavailable, many parameters that determine the probability density functions (PDF) of observations are unknown. Therefore, the unknown parameters are replaced with their maximum likelihood (ML) estimates, and this method is the generalized likelihood ratio test (GLRT). The test statistics can be expressed as $$L'_{ML}(z_n) = -\frac{2}{N}\log(L_{ML}(z_n)) = \frac{1}{N}\sum_{k=n}^{n+N-1}\frac{1}{\sigma_a^2}\left\|y_k^a - g\frac{\bar{y}^\alpha}{\|\bar{y}^\alpha\|}\right\|^2 + \frac{1}{\sigma_\omega^2}\|y_k^\omega\|^2 \quad (2)$$

where $y_k^a$ and $y_k^\omega$ are the accelerometer and the gyroscope data at time index k, respectively, $\bar{y}^\alpha$ is the averaged value of the N consecutive accelerometer data, $\sigma_a$ and $\sigma_\omega$ are related to the white noise level of the accelerometer and the gyroscope, and g is gravity.

We can then state the GLRT as: choose $H_1$ if $$L'_{ML}(Z_n) < \gamma \quad (3)$$

where $\gamma$ is the threshold to be determined.

Adaptive Threshold Determination

One or more embodiments are directed to processes and device configurations for an adaptive threshold determination. For different gait patterns, the distributions of $z_n$ are also different, and therefore different thresholds are needed. In this section, we derive an adaptive threshold based on time dependent prior information and cost function.

There are three general goals of adaptive threshold. 1) Limit the probability of false alarm. False alarm happens if the detector determines the IMU is stationary while the foot is actually moving. False alarm will cause the Kalman filter to erroneously set the velocity close to zero, which greatly degrade the results of navigation. 2) Minimize the probability of missed detections. Stance phase is the time period when zero-velocity information can be utilized to suppress the navigation error growth. A missed detection will reduce the chance of compensation, and, therefore, increase the overall navigation error. 3) Adjust the threshold parameters automatically to fit different gait dynamics and maintain a proper amount of zero-velocity updates.

Figure 11:
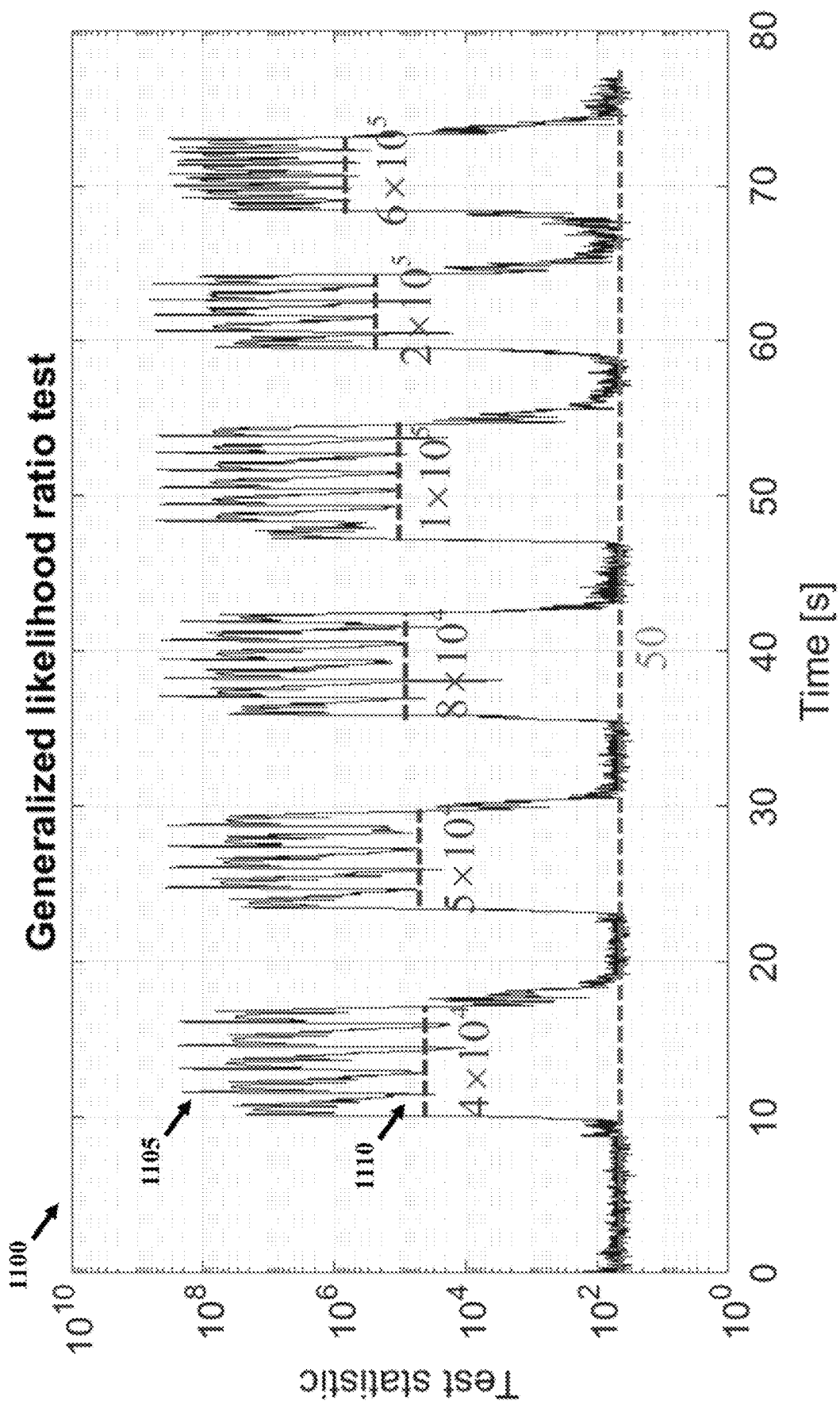
FIG. 11 illustrates a generalized likelihood ratio for test statistics generated from inertial measurement unit (IMU) data from various different walking and running paces according to one or more embodiments.

FIG. 11 shows a typical test statistic $L'_{ML}$ (zn) with different gait dynamics over time as 1100. There are six different gait dynamics shown in FIG. 11, such as gait dynamic 1105, corresponding to walking at the pace of 80, 90, 100, 110, and 120 steps per minute, and running at the pace of 160 steps per minute, respectively. A high statistic indicates that the IMU is moving while a lower value shows that the IMU is close to a stationary state. FIG. 11 shows that the test statistic is around 100 when the foot is actually stationary (represented by the time period between the six movements). The dashed lines 1110 are the averaged values of test statistics during the stance phase related to different gait dynamics, ranging from the lowest of $4\times10^4$ to the highest of $6\times10^5$. The purpose of the adaptive threshold is to capture differences caused by different paces and patterns such as walking, running, jumping, and even crawling. Note that these values are much higher than the test statistic when the foot is stationary on the floor, indicating that the foot is not absolutely stationary even during the stance phase. As a result, an excessive use of zero-velocity update will cause degradation to the overall navigation accuracy.

The Bayesian likelihood ratio test states that the threshold can be expressed as $$\gamma = \frac{p(H_0)}{p(H_1)} \cdot \frac{c_{10} - c_{00}}{c_{01} - c_{11}} \quad (4)$$

where $p(H_0)/p(H_1)$ is the prior probability of the hypotheses, $c_{00}$ is the cost function of correctly detecting the swing phase, $c_{11}$ is the cost function of correctly detecting the stance phase, $c_{10}$, is the cost function of a false alarm, and con is the cost function of a missed detection. We assume a uniform prior probability and zero cost function for correct detections of the swing phase and stance phase. Thus, the threshold is only the ratio of the cost function of false alarm and missed detection.

The missed detection is the case where the detector determines that the IMU is moving during the stance phase. The associated cost is time-dependent by its nature, since the navigation error accumulates as a polynomial with respect to time without any error suppression. The order of the polynomial is related to many factors, such as the time duration, IMU noise level, and dynamics of motion. Therefore, we believe that it is proper to assume a polynomial cost function for missed detection instead of an exponential one reported in. On the other hand, the cost of a false alarm is relatively time-independent compared to a missed detection. Therefore, we can assume a constant cost for the false alarm and a polynomial cost for missed detection. We define the ratio of the cost of a false alarm to the cost of a missed detection to be $$\gamma = \frac{c_{10}}{c_{01}} = \alpha_1 \cdot \Delta t^{-\theta_l} \quad (5)$$

where $\Delta t$ is the time difference between the previous ZUPT and the current time step, and $\alpha_1$ and $\theta_1$ are design parameters to be decided. The threshold $\gamma'$ can be expressed as $$\gamma' = -\frac{2}{N}\log(\gamma) = -\frac{2}{N}(\log(\alpha_1) - \theta_1 \cdot \log(\Delta t)) \triangleq \theta \cdot \log(\Delta t) + \alpha. \quad (6)$$

$\gamma'$ is small immediately after detection of the last stance phase since $\Delta t$ is small. The physical interpretation is that the probability of detecting another stance phase is low, according to (6), since we do not expect two stance phases very close to each other.

Another advantage of polynomial cost can be shown from (6). Note that (6) would be in the form of $\theta \cdot \Delta t + \alpha$, if exponential cost were to be used. For normal gait patterns, the range of $\Delta t$ is typically around one second. The slope of $\log(\Delta t)$, which is associated with the polynomial cost, is similar to that of $\Delta t$, which is in turn associated with the exponential cost, when $\Delta t$ is around one second, but the slope is much larger if $\Delta t$ is smaller than one second. Therefore, a similar performance of stance phase detection could be expected with a better robustness against false alarm in between the two stance phases. The threshold $\gamma'$ will increase at a speed defined by $\theta$ as $\Delta t$ increases, and a defines the overall level of the threshold. Ideally, $\theta$ would be defined such that $\gamma'$ increases to the level of the test statistic during the stance phase (indicated by the dashed lines 1110 in FIG. 11), when the next stance phase would actually start. This requires an estimation of the level of the test statistic during the stance phase, which is directly related to the gait frequency. In this application instead of predefining the gait frequency as in which is unrealistic in real navigation applications, or applying the Fourier transform to extract the gait frequency as in whose response to frequency change is slow, embodiments can take advantage of the shock level that the IMU experiences during the heel strike as an indicator to estimate the real-time gait frequency.

As the step pace increases, the minimum test statistics increases, as well as the shock level that the IMU experiences during the heel strike. The relation between the shock level and the minimum test statistics is shown as 1200 in FIG. 12. The dots 1205 correspond to data from different gait cycles and the dashed line 1210 is a fitted curve. An exponential formula can be used to approximate the relation, and the parameter $\theta$ in (6) can be defined as $$\theta = \text{\euro} \cdot \exp(0.0307 \times \text{Shock} + 8.6348) \tag{7}$$

where Shock is the shock level during the heel strike, $\text{\euro}$ is the parameter that can be adjusted to achieve a proper length of the stance phase, (set to be 3.5 for illustration purposes only in this application), and $\alpha$ can also be adjusted accordingly.

Advantages of using shock level during the heel strike to extract gait frequency include the following. 1) No prior knowledge of the gait frequency is needed. 2) Ability to track continuously changing gait frequency with faster response than Fourier transform. 3) Shock level can be directly measured and the required computational power is much lower than machine learning methods.

Figure 13:
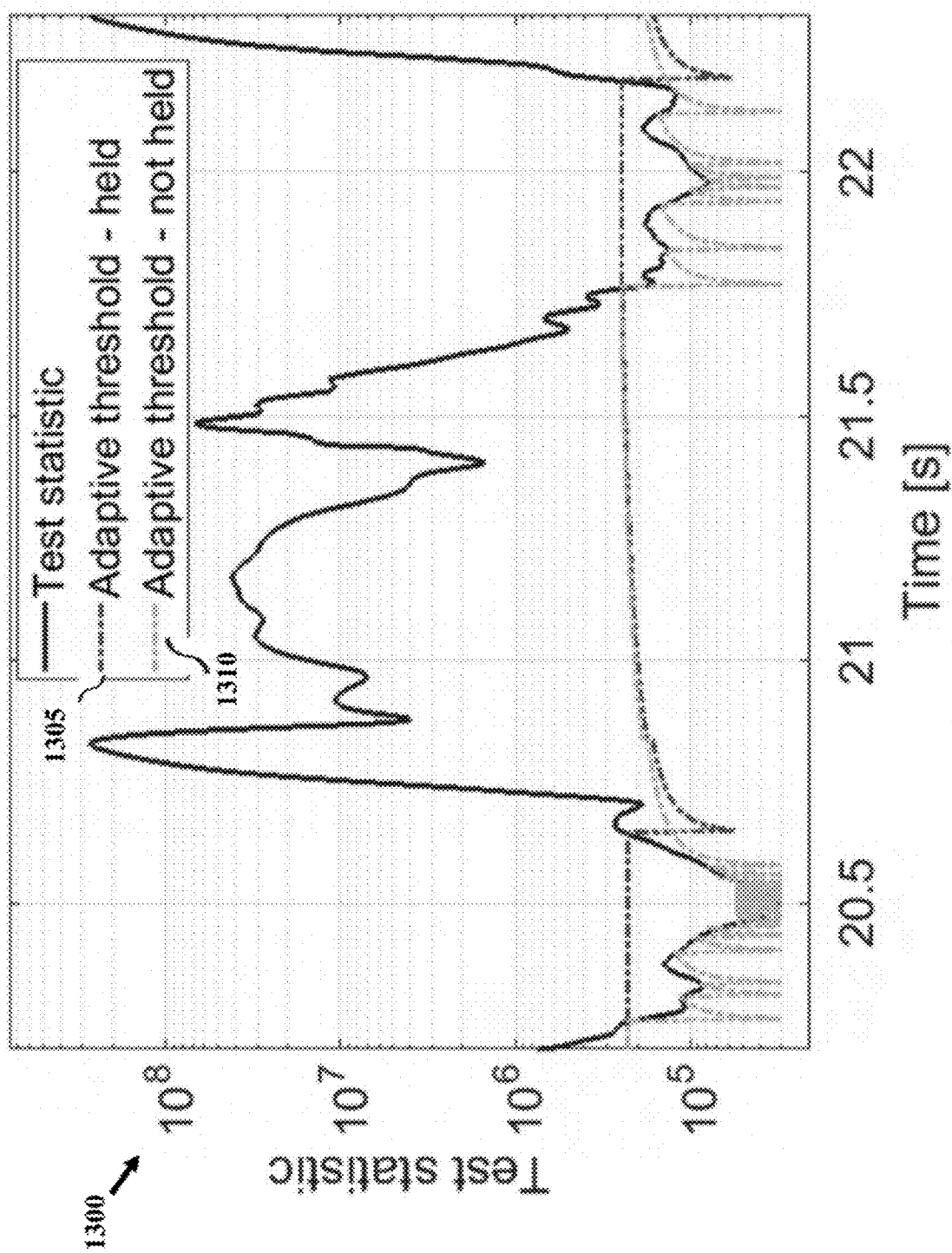
FIG. 13 illustrates a test statistic, a non-held adaptive threshold, and a held adaptive threshold which is held during the detected stance phase according to one or more embodiments.

To ensure that enough zero-velocity updates could be implemented to suppress the navigation error, threshold $\gamma'$ is artificially held until it becomes smaller than the test statistic again, instead of allowing it to drop back as (6) indicates. The effect of the holding is shown in FIG. 13 as 1300 with data representing adaptive threshold that is held as 1305 and an adaptive threshold that is not held as 1310. The artificial holding enables us to detect the whole stance phase instead of just some time instances in the stance phase.

Experimental Verification

The methods of adaptive threshold described in this application are effective in reducing navigation errors and improving accuracy without adding additional sensors to the system. Computational complexity of detecting the gait frequency is also lower than machine learning methods because the shock level of the heel can be directly measured, and the gait frequency can be directly correlated to the shock level. Gait frequency can be determined based on the period of time between peaks in acceleration produced by the heel strikes.

According to one embodiment, an IMU (e.g., IMU 101, IMU 201, etc.) is rigidly mounted above the forefoot and the sampling rate of the IMU is 400 Hz. Other mounting locations may be used, including under the toe, or any location between the heel and toe, or embedded in footwear. Sampling rates from 100 Hz to 800 Hz provide acceptable accuracy. Other sampling rates may also be used, including any sampling rate that satisfies the Nyquist theorem in capturing the heel strike without aliasing. Higher sampling rates provide higher navigation accuracy, but require handling larger amounts of data. Selecting an appropriate sampling rate involves a trade-off between accuracy and data processing requirements.

Figure 14A:
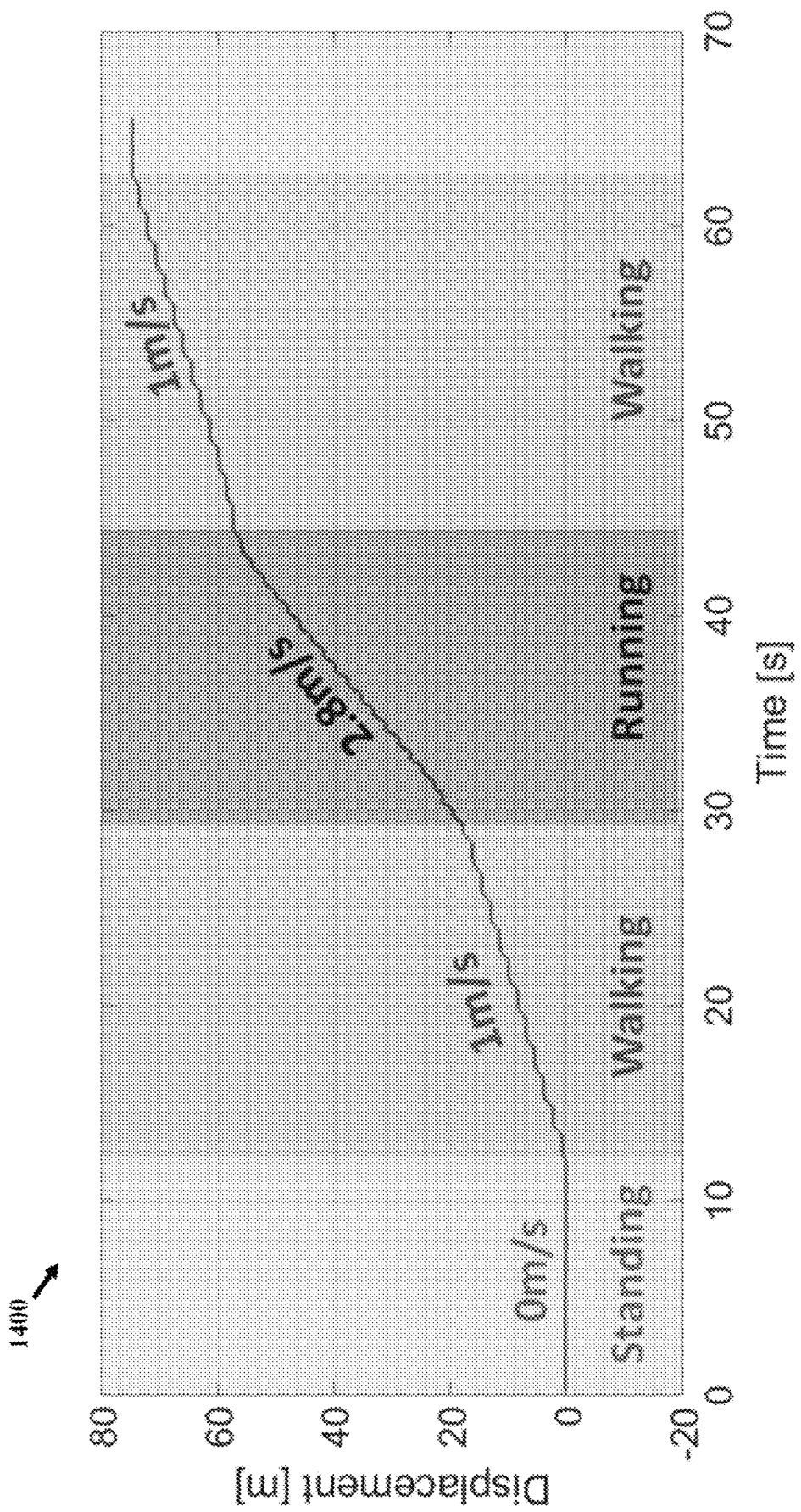
FIG. 14A illustrates time and displacement for standing, walking, and running pedestrian inertial navigation scenarios according to one or more embodiments.
Figure 14B:
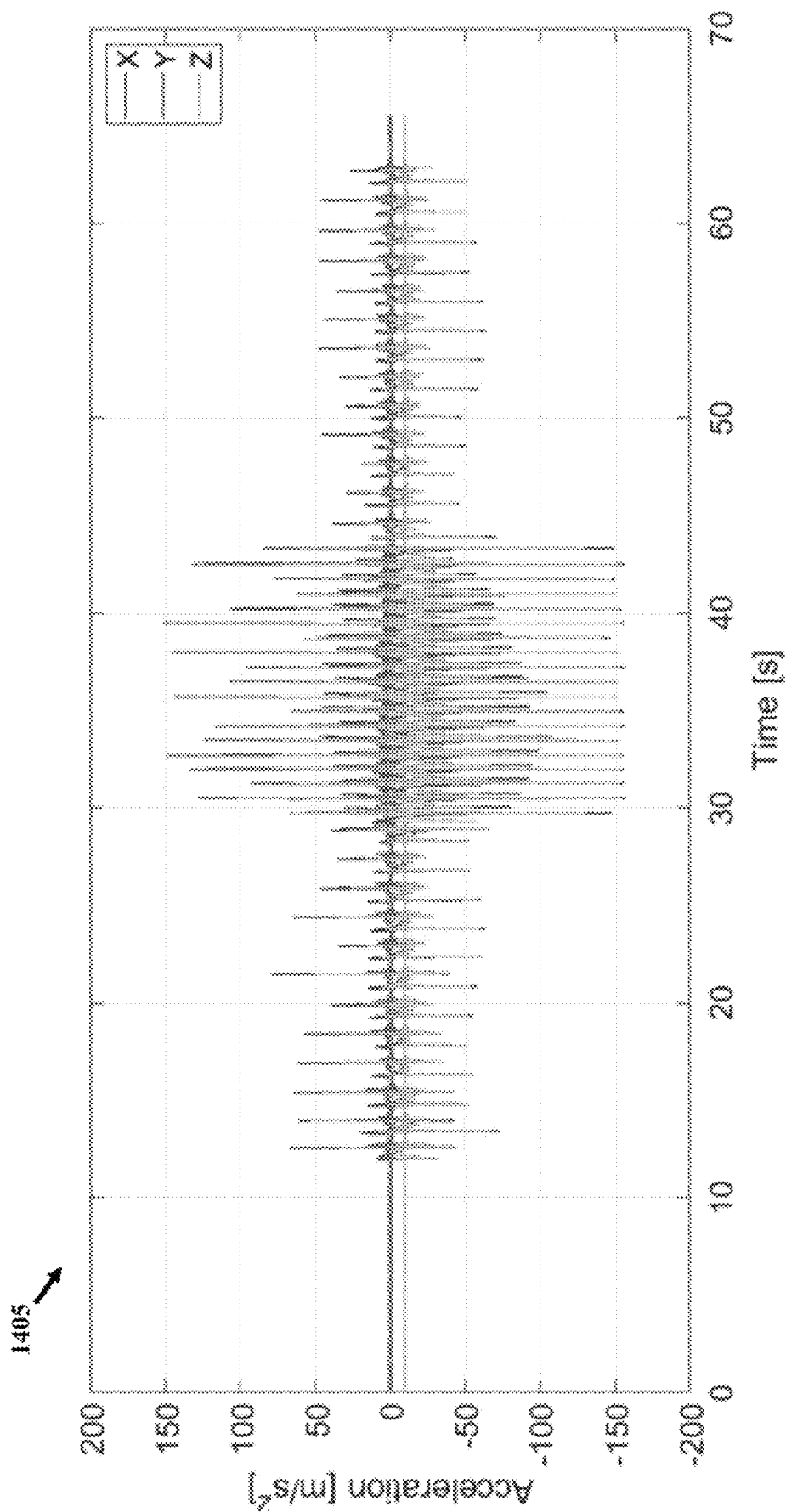
FIG. 14B illustrates a shock level as acceleration over time corresponding to the standing, walking, and running pedestrian inertial navigation scenarios of FIG. 14A according to one or more embodiments.
Figure 14C:
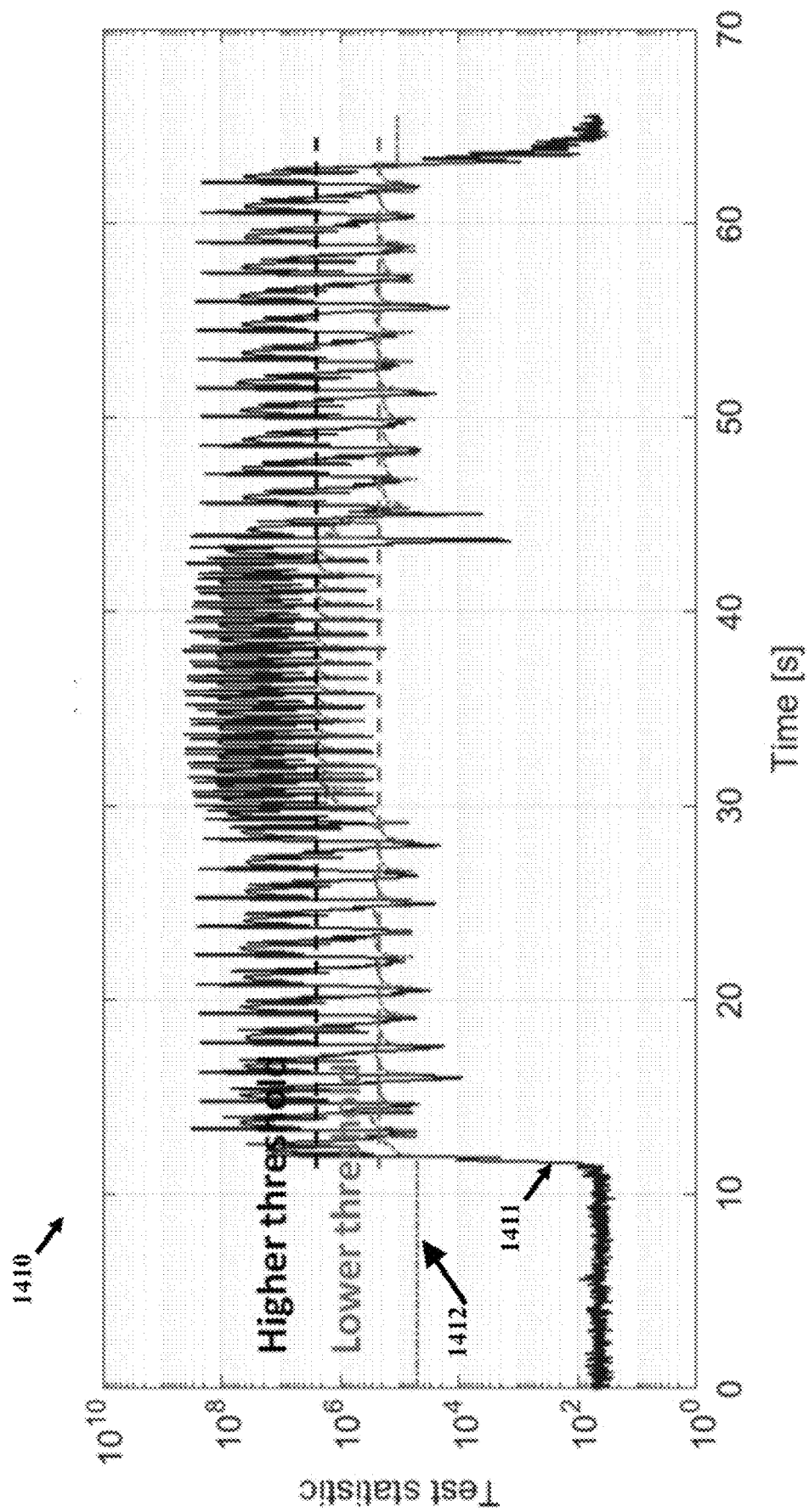
FIG. 14C illustrates adjusting the threshold between a lower threshold and a higher threshold corresponding to the standing, walking, and running pedestrian inertial navigation scenarios of FIG. 14A according to one or more embodiments.

In testing the effectiveness of the disclosed methods of adaptive threshold, during the navigation, an agent first stood for about 12 seconds, then walked at a pace of 80 steps per minute for about 15 seconds. It was followed by running at a pace of 160 steps per minute for about 15 seconds and walking for another 20 seconds. At last, the agent stood for about 5 seconds. The position propagation, accelerometer data, GLRT, and the navigation results are presented in FIGS. 14A-14D. FIG. 14A shows graph 1400 of velocity and the velocity difference between walking and running. FIG. 14B shows the specific force 1405 of the IMU. A much higher shock level of about 150 m/s$^2$ during running was observed, exceeding the level of about 50 m/s$^2$ during walking. FIG. 14C shows graph 1410 including test statistics 1411 (solid line) and the adaptive threshold 1412 (dashed line). The minimum test statistics for walking and running were about $2 \times 10^5$ (lower threshold) and $2 \times 10^6$ (higher threshold), respectively. The adaptive threshold successfully captures the changes in navigation dynamics.

Figure 14D:
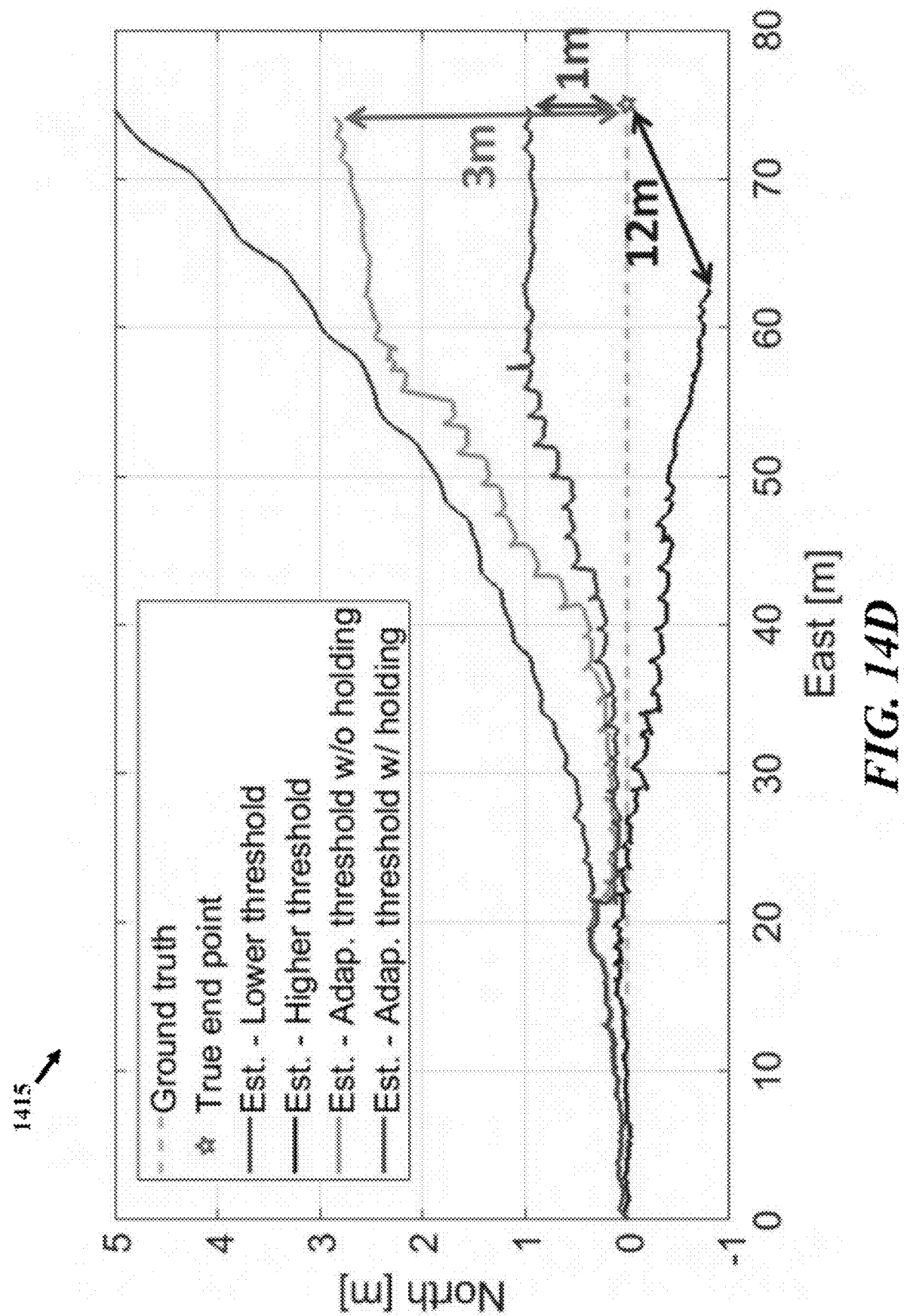
FIG. 14D illustrates an estimated position using the lower threshold, the higher threshold, a non-held adaptive threshold, and a held adaptive threshold in comparison to a ground truth for the pedestrian navigation of FIG. 14A according to one or more embodiments.

FIG. 14D shows comparison 1415 of estimated trajectories with the adaptive threshold with and without artificial holding, with the lower fixed threshold shown in FIG. 14C, and with the higher fixed threshold shown in FIG. 14C. The stance phase during running could not be detected with lower threshold. Thus, the estimated trajectory drifted away after the agent started running. Too many zero-velocity updates were imposed during walking with higher threshold. Therefore, the estimated trajectory was shorter than the ground truth, causing a large navigation error of 12 meters. The navigation error was reduced to about 1 meter with the adaptive threshold.

Figure 15:
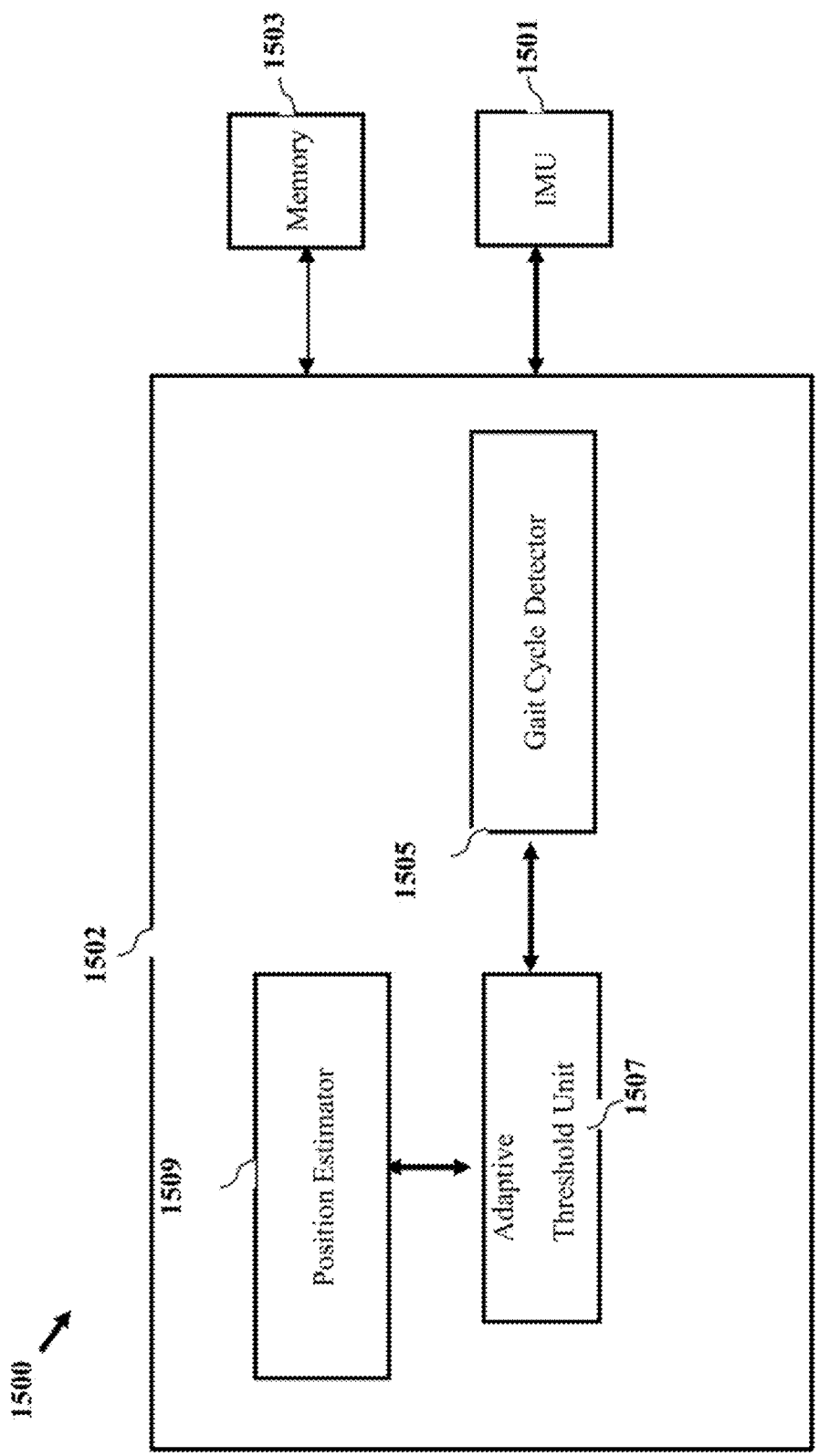
FIG. 15 illustrates a pedestrian inertial navigation system including a zero velocity detector according to one or more embodiments.

FIG. 15 illustrates an adaptive threshold aided pedestrian inertial navigation system 1500 comprising an inertial measurement unit (IMU) 1501 and a processor 1502. The IMU 1501 may include one or more accelerometers, gyroscopes or other inertial measurement sensors. Data from IMU 1501 and data used and produced in the navigation position estimation is stored in memory 1503. Memory 1503 may be any computer readable storage device. The system 1500 also includes a gait cycle detector 1505. According to some embodiments, the gait cycle detector 1505 is configured to detect the gait frequency based on an accelerometer peaks produced by heel strikes. An adaptive threshold unit 1507 is configured to adapt the zero-velocity update threshold based on the detected gait cycle. The position estimator 1509 is configured to estimate the navigation position based on the adapted zero-velocity update threshold.

Figure 16:
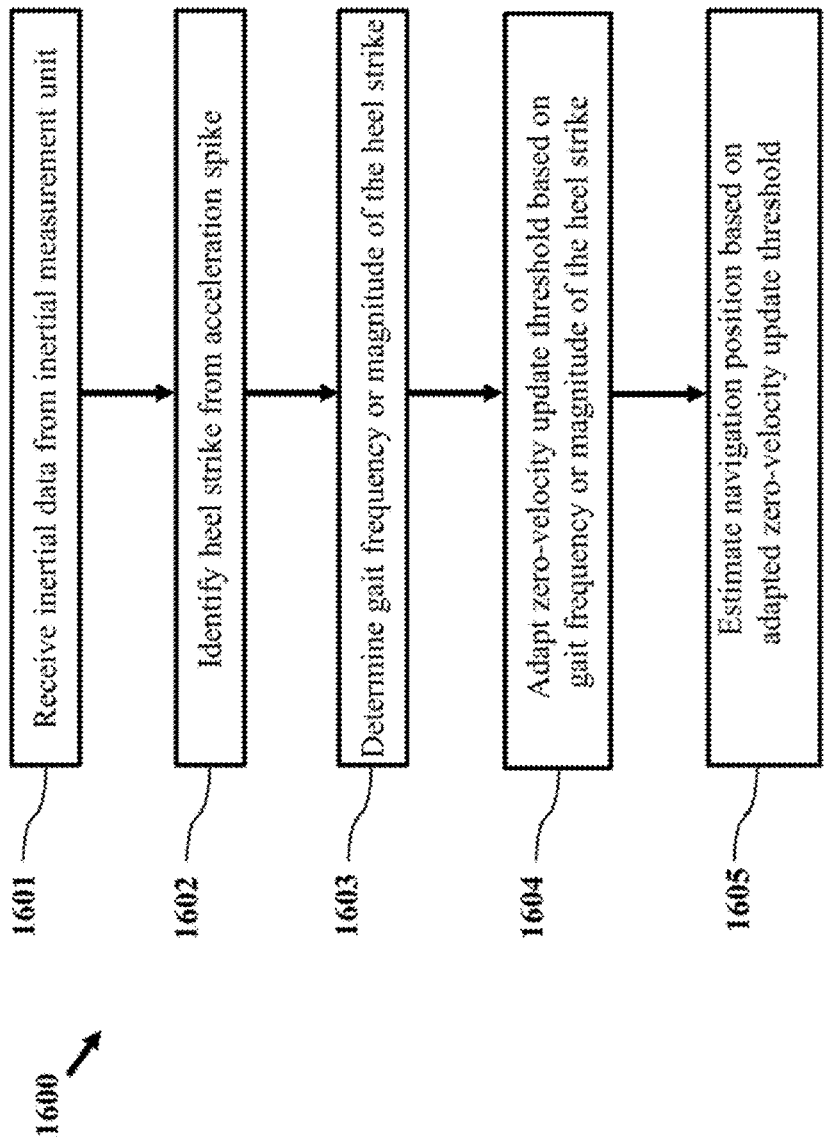
FIG. 16 depicts a process for dynamically adjusting a threshold in a zero velocity detector according to one or more embodiments.

FIG. 16 illustrates a method for dynamically adjusting a threshold in a zero velocity detector according to one or more embodiments. Process 1600 includes receiving inertial data at block 1601 from an inertial measurement unit (e.g., IMU 1501). Inertial data may be produced by an accelerometer, a gyroscope or both. According to an embodiment, a method receives inertial data from three accelerometers and three gyroscopes. At block 1602, a heel strike may be identified from an acceleration spike in IMU data. Detection of a heel strike may be used for partitioning the inertial data based on at least one identified heel strike in the inertial data. Each heel strike identified may be based on a peak in the inertial data. At block 1603, the process 1600 includes determining the gait frequency or the magnitude of the heel strike. The magnitude of the heel strike may be determined directly from the IMU data. The gait frequency may be determined based on the period of time between heel strikes detected as peaks in the accelerometer data. Heel strikes may be identified to determine a stance phase.

Figure 12:
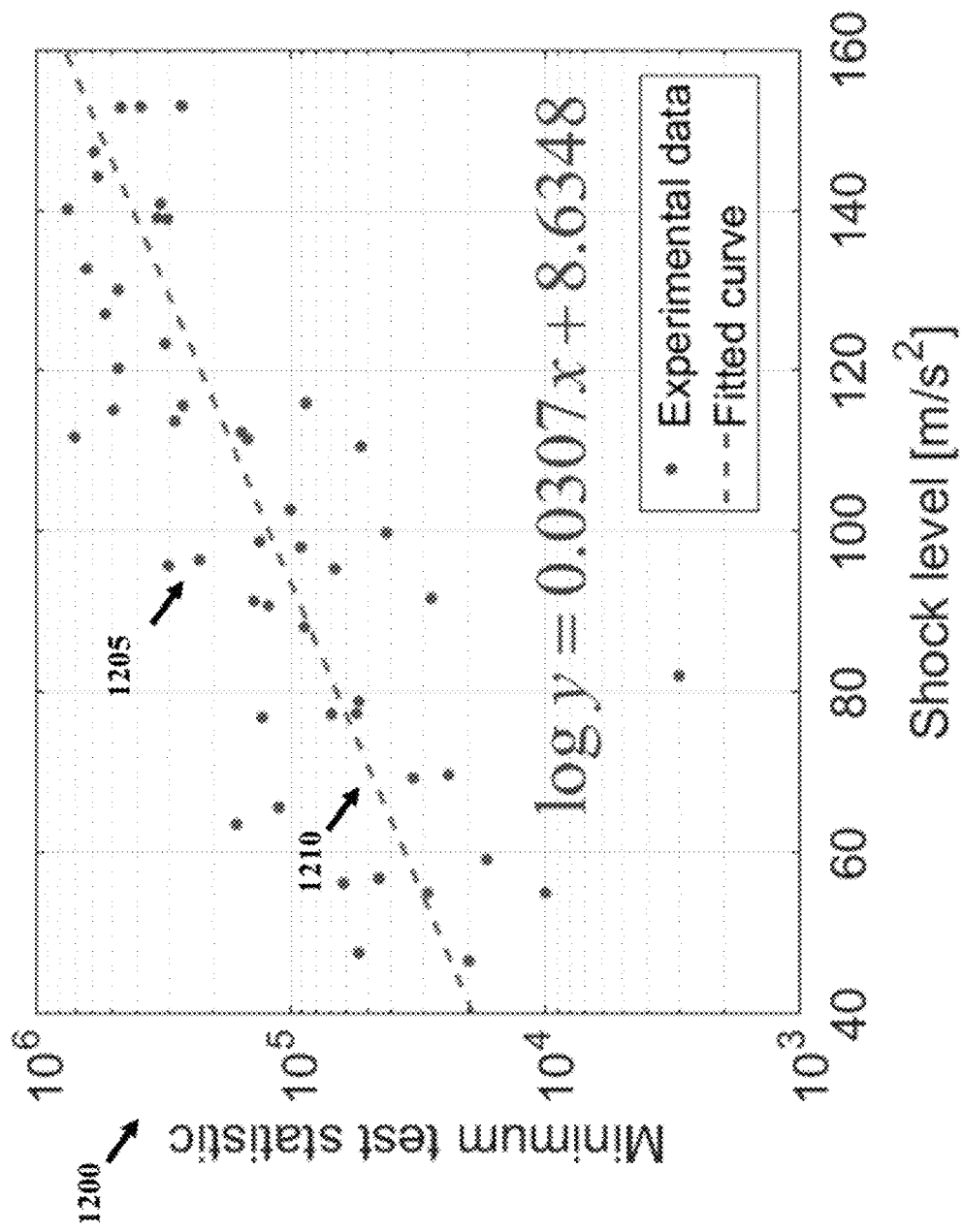
FIG. 12 is a scatter plot illustrating a relationship between shock level and minimum test statistics related to IMU data according to one or more embodiments.

The magnitude of the heel strike has a relationship to the gait frequency and to the minimum test statistic used to determine the adaptive zero-velocity update threshold. A relationship between the magnitude of the heel strike and the minimum test statistic is illustrated in FIG. 12. Therefore, the adaptive zero-velocity update threshold may be determined based on the magnitude of the shock level during the heel strike. Alternatively, the adaptive zero-velocity update threshold may be determined based on the gait frequency. Process 1600 may include detecting the gait frequency based on detection of a toe-off peak produced by one or more gyroscopes. The gait frequency correlates with the magnitude of inertial data, or shock level, produced during the stance phase. Therefore a fixed threshold will tend to miss detection of the stance phase or generate a false positive detection of the stance phase. At block 1604, process 1600 adapts/adjusts the zero-velocity update threshold based on the gait frequency. Generally, as gait frequency increases, the zero-velocity update threshold may also be increased. At step 1605, the system estimates the navigation position based on the adapted zero-velocity update threshold.

This application describes an adaptive threshold for ZUPT-aided pedestrian inertial navigation, enabling ZUPT-aided pedestrian inertial navigation with continuously changing gait frequency. The method utilizes a Bayesian approach and the dynamics relating the shock level of the IM and the test statistic during the stance phase. With the adaptive threshold implemented, the navigation error is reduced by 12 times compared to a fixed threshold, with only a marginal increase in the system complexity to extract the shock level during the gait cycle.

While floor type detection may be implemented independently of adaptive threshold based on gait frequency or magnitude of heel strikes, the two concepts may also be combined for increased accuracy in pedestrian inertial navigation systems. In combining the disclosed concepts, the multiple model Kalman filter may be augmented to improve accuracy for different magnitudes of the heal strike or different gait frequencies. The multiple model Kalman filter may be configured to adapt the zero-velocity update threshold for various gait frequencies for various floor types. One of ordinary skill in the art will understand that the disclosed embodiments may be implemented independently or in combination at varying levels of complexity without departing from the spirit and scope of the disclosed embodiments.

While this disclosure has been particularly shown and described with references to exemplary embodiments thereof, it will be understood by those skilled in the art that various changes in form and details may be made therein without departing from the scope of the claimed embodiments.

What is claimed is:

1. A method for pedestrian inertial navigation, the method comprising:
   receiving, by a processor, inertial data from an inertial measurement unit, wherein the inertial data is generated by the inertial measurement unit and the inertial data includes at least one of accelerometer data for a plurality of axes and gyroscope data for a plurality of axes, and wherein the inertial measurement unit is mounted to a foot of a user;
   partitioning, by the processor, the inertial data into a plurality of partitions, wherein each partition of the inertial data is a full gait cycle;
   reducing, by the processor, dimensionality of the plurality of partitions using principle component analysis, wherein reducing dimensionality includes generating an independent linear function for inertial data received from the inertial measurement unit and using a validation approach to determine an output dimension of the principle component analysis;
   identifying, by the processor, a floor type of each partition, wherein the floor type of each partition is determined using an artificial neural network;
   adapting, by the processor, one or more inertial navigation parameters for each partition using identified floor type, wherein a zero-velocity update threshold is adapted for a gait frequency and for floor type; and
   estimating, by the processor, a navigation position of the inertial measurement unit based on adapted inertial navigation parameters.

2. The method of claim 1, wherein mounted to a foot of a user includes mounting to at least one of a forefoot, above the forefoot, under a toe, between a heel and toe, and embedded in footwear of the user.

3. The method of claim 1, wherein partitioning of the inertial data is based on at least one identified toe-off, each toe-off identified in the inertial data by identifying a peak in the inertial data.

4. The method of claim 1, wherein partitioning the inertial data includes partitioning based on at least one identified heel strike in the inertial data, each heel strike identified based on a peak in the inertial data.

5. The method of claim 4, further comprising determining a gait frequency based on a period of time between heel strikes, and wherein estimating the navigation position is based on the adapted zero-velocity update threshold.

6. The method of claim 4, wherein the at least one heel strike is identified to determine a stance phase.

7. The method of claim 1, wherein a shock level of the inertial measurement unit during a heel strike is an indicator of gait frequency.

8. The method of claim 1, wherein identifying a floor type includes using an artificial neural network trained by backpropagation with mini-batch gradient to identify at least one floor type based on floor hardness, motion of a foot, gait pattern and foot stability.

9. The method of claim 1, wherein adapting the one or more inertial navigation parameters includes modifying a navigation parameter using at least one of:
   a velocity during a stance phase; and
   an uncertainty corresponding to the velocity.

10. The method of claim 1, wherein estimating a navigation position of the inertial measurement unit based on adapted inertial navigation parameters includes determining a navigation path relative to a starting point, wherein position measurements of the IMU are adapted to determine position of a user, wherein estimating the navigation position is based on the adapted zero-velocity update threshold.

11. The method of claim 1, further comprising:
   maintaining a zero-velocity update threshold while inertial data is below a threshold, and
   reducing the threshold in response to the inertial data exceeding the threshold.

12. A device configured for pedestrian inertial navigation, the device comprising:
   an inertial measurement unit configured to generate inertial data; and
   a processor coupled to the inertial measurement unit, the processor configured to
      receive inertial data from an inertial measurement unit, wherein the inertial data is generated by the inertial measurement unit and the inertial data includes at least one of accelerometer data for a plurality of axes and gyroscope data for a plurality of axes, and wherein the inertial measurement unit is mounted to a foot of a user,
      partition the inertial data into a plurality of partitions, wherein each partition of the inertial data is a full gait cycle,
      reduce dimensionality of the plurality of partitions using principle component analysis, wherein reducing dimensionality includes generating an independent linear function for inertial data received from the inertial measurement unit and using a validation approach to determine an output dimension of the principle component analysis, identify a floor type of each partition, wherein the floor type of each partition is determined using an artificial neural network, adapt one or more inertial navigation parameters for each partition using identified floor type, wherein a zero-velocity update threshold is adapted for a gait frequency and for floor type, and estimate a navigation position of the inertial measurement unit based on adapted inertial navigation parameters.

13. The device of claim 12, wherein mounted to a foot of a user includes mounting to at least one of a forefoot, above the forefoot, under a toe, between a heel and toe, and embedded in footwear of the user.

14. The device of claim 12, wherein partitioning of the inertial data is based on at least one of an identified toe-off and an identified heel strike.

15. The device of claim 12, wherein the processor is further configured to determine a gait frequency based on a period of time between heel strikes.

16. The device of claim 12, wherein shock level of the inertial measurement unit during a heel strike is an indicator of gait frequency.

17. The device of claim 12, wherein identifying a floor type includes using an artificial neural network trained by backpropagation with mini-batch gradient to identify at least one floor type based on floor hardness, motion of a foot, gait pattern and foot stability.

18. The device of claim 12, wherein adapting the one or more inertial navigation parameters includes modifying a navigation parameter using at least one of:
a velocity during a stance phase; and
an uncertainty corresponding to the velocity.

19. The device of claim 12, wherein estimating a navigation position of the inertial measurement unit based on adapted inertial navigation parameters includes determining a navigation path relative to a starting point using, wherein position measurements of the IMU are adapted to determine position of a user.

20. The device of claim 12, wherein the processor is further configured to:
maintain a zero-velocity update threshold while the inertial data is below the threshold, and
reduce the threshold in response to the inertial data exceeding the threshold.

* * * * *